US011407851B2

(12) United States Patent
Nash et al.

(10) Patent No.: US 11,407,851 B2
(45) Date of Patent: *Aug. 9, 2022

(54) CHEMICALLY MODIFIED SHAPE MEMORY POLYMER EMBOLIC FOAMS WITH INCREASED X-RAY VISUALIZATION

(71) Applicant: The Texas A&M University System, College Station, TX (US)

(72) Inventors: Landon D. Nash, Sunnyvale, CA (US); Kendal P. Ezell, Tomball, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/465,555

(22) PCT Filed: Dec. 1, 2017

(86) PCT No.: PCT/US2017/064355
§ 371 (c)(1),
(2) Date: May 30, 2019

(87) PCT Pub. No.: WO2018/102779
PCT Pub. Date: Jun. 7, 2018

(65) Prior Publication Data
US 2020/0017625 A1 Jan. 16, 2020

Related U.S. Application Data

(60) Provisional application No. 62/429,148, filed on Dec. 2, 2016.

(51) Int. Cl.
*C08G 18/32* (2006.01)
*C08G 18/38* (2006.01)
(Continued)

(52) U.S. Cl.
CPC ..... *C08G 18/3275* (2013.01); *C08G 18/3206* (2013.01); *C08G 18/3215* (2013.01);
(Continued)

(58) Field of Classification Search
CPC .. C08G 18/3802–3804; C08G 18/3814; C08G 18/3817
See application file for complete search history.

(56) References Cited

U.S. PATENT DOCUMENTS 4,722,344 A * 2/1988 Cambron ............... A61L 29/06
600/435
5,319,905 A 6/1994 Szirtes
(Continued)

FOREIGN PATENT DOCUMENTS

CN 101392048 A 3/2009
CN 101747486 A 6/2010
(Continued)

OTHER PUBLICATIONS

Kiran, S. et al. Synthesis and characterization of iodinated polyurethane with inherent radiopacity. Biomaterials, 2009, 30, 5552-5559. Available online Jul. 12, 2009. (Year: 2009).*
(Continued)

*Primary Examiner* — Stephen E Rieth
(74) *Attorney, Agent, or Firm* — Trop, Pruner & Hu, P.C.

(57) ABSTRACT

An embodiment includes a system comprising: an iodine containing thermoset open-cell shape memory polymer (SMP) foam that is x-ray visible; wherein (a) the SMP foam is configured to expand from a compressed secondary state to an expanded primary state in response to thermal stimulus, (b) the SMP foam is a poly(urethane-urea-amide). Other embodiments are described herein.

14 Claims, 16 Drawing Sheets

(51) Int. Cl.
*C08G 18/50* (2006.01)
*C08K 7/02* (2006.01)
*C08K 3/08* (2006.01)
*C08G 18/73* (2006.01)
*C08K 5/00* (2006.01)
*C08K 5/52* (2006.01)

(52) U.S. Cl.
CPC ..... *C08G 18/3821* (2013.01); *C08G 18/3897* (2013.01); *C08G 18/5018* (2013.01); *C08G 18/73* (2013.01); *C08G 2110/005* (2021.01); *C08G 2280/00* (2013.01); *C08K 3/08* (2013.01); *C08K 5/0066* (2013.01); *C08K 5/52* (2013.01); *C08K 7/02* (2013.01); *C08K 2003/0887* (2013.01)

(56) References Cited

U.S. PATENT DOCUMENTS

| | | | |
|---|---|---|---|
| 6,599,448 | B1 | 7/2003 | Ehrhard et al. |
| 8,888,675 | B2 | 11/2014 | Stankus et al. |
| 10,485,903 | B2* | 11/2019 | Maitland ................. A61F 2/945 |
| 2010/0262182 | A1* | 10/2010 | Moszner ............ A61K 49/0442 264/210.8 |
| 2012/0158034 | A1* | 6/2012 | Wilson ............... A61B 17/1214 606/192 |
| 2013/0253086 | A1* | 9/2013 | Wilson ............... C08G 18/3851 521/166 |
| 2014/0142207 | A1 | 5/2014 | Singhal et al. |
| 2015/0119706 | A1 | 4/2015 | Zheng-Rong |
| 2016/0270961 | A1 | 9/2016 | Maitland et al. |

FOREIGN PATENT DOCUMENTS

| | | |
|---|---|---|
| CN | 101842120 A | 9/2010 |
| CN | 101945672 A | 1/2011 |
| CN | 102428068 A | 4/2012 |
| CN | 102803365 A | 11/2012 |
| CN | 102844521 A | 12/2012 |
| JP | H03231964 A | 10/1991 |
| JP | H06506494 A | 7/1994 |
| JP | H0723323234 A | 9/1995 |
| JP | 2006-070232 | 3/2006 |
| JP | 2008524410 A | 7/2008 |
| JP | 2008239725 A | 10/2008 |
| JP | 2014517120 A | 7/2014 |
| KR | 20100112842 A | 10/2010 |
| WO | 2004063088 A1 | 7/2004 |
| WO | 2015004669 A1 | 1/2015 |
| WO | WO2016149070 | 9/2016 |
| WO | 2016191492 A1 | 12/2016 |

OTHER PUBLICATIONS

Fisher Scientific. Diatrizoic Acid Information. https://www.fishersci.com/shop/products/diatrizoic-acid-tci-america/D146225G. As viewed on Aug. 10, 2021. (Year: 2021).*

International Searching Authority, "Notification of Transmittal of the International Search Report and the Written Opinion of the International Searching Authority," dated Mar. 19, 2018, in International application No. PCT/US2017/064355.

International Searching Authority, "International Preliminary Report on Patentability," dated Jun. 4, 2019, in International application No. PCT/US2017/064355.

Gaba, R.C., et al., "Embolization of Intracranial Aneurysms With Hydrogel-Coated Coils Versus Inert Platinum Coils Effects on Packing Density, Coil Length and Quantity, Procedure Performance, Cost, Length of Hospital Stay, and Durability of Therapy," Stroke, 2006, pp. 1-8.

O'Hare, A., et al., "HydroCoils, occlusion rates, and outcomes: a large single-center study," American Journal of Neuroradiology, 2010, pp. 1-6.

Maitland, D.J., et al., "Prototype laser-activated shape memory polymer foam device for embolic treatment of aneurysms," J Biomed Opt, 2007. pp. 1-3.

Singhal, P., et al., "Ultra low density and highly crosslinked biocompatible shape memory polyurethane foams," Journal of Polymer Science Part B: Polymer Physics, 2012, pp. 1-27.

Rodriguez, J.N., et al., "In vivo response to an implanted shape memory polyurethane foam in a porcine aneurysm model," Journal of Biomedical 1-23.Materials Research Part A, 2014, pp. 1-23.

Szikora, I., et al., "Histopathologic evaluation of aneurysms treated with Guglielmi detachable coils or matrix detachable microcoils," American journal of neuroradiology, 2006, pp. 1-7.

Boyle, A.J., et al., "In vitro and in vivo evaluation of a shape memory polymer foam-over-wire embolization device delivered in saccular aneurysm models," Journal of Biomedical Materials Research Part B: Applied Biomaterials, 2015, pp. 1-21.

Hwang, W., et al., "Estimation of aneurysm wall stresses created by treatment with a shape memory polymer foam device," Biomech Model Mechanobiol, 2012, pp. 1-34.

Rodriguez, J., et al., "Opacification of Shape Memory Polymer Foam Designed for Treatment of Intracranial Aneurysms," Annals of Biomedical Engineering, 2012, pp. 1-25.

Hasan, S.M., et al., "Modification of shape memory polymer foams using tungsten, aluminum oxide, and silicon dioxide nanoparticles," RSC Advances, 2016, pp. 1-22.

Hasan, S.M., et al., "Tungsten-loaded SMP foam nanocomposites with inherent radiopacity and tunable thermo-mechanical properties," Polymers for Advanced Technologies, 2016, pp. 1-19.

Werner Krause, et al, "Chemistry of X-Ray Contrast Agents, in Contrast Agents II," Topics in Current Chemistry, vol. 222, Springer-Verlag Berlin Heidelberg 2002, 44 pages.

Nirmala R. James, et al., "Polyurethanes With Radiopaque Properties," Jul. 18, 2005, 7 pages.

Landon D. Nash, et al., "Increased X-ray Visualization of Shape Memory Polymer Foams by Chemical Incorporation of Iodine Motifs," Aug. 20, 2017, 16 pages.

European Patent Office, Extended European Search Report dated Mar. 11, 2020 in European patent application No. 17 876 750.5, 7 pages total.

China Patent Office, Office Action dated Jan. 22, 2021 in Chinese Patent Application No. 201780074595.7 (38 pages).

Liang et al., Clinical Summary and Imaging Diagnosis of Modern Diseases, 1st Edition, 2014, pp. 69-70.

Small et al., "Shape Memory Polymer Stent with Expandable Foam: A New Concept for Endovascular Embolization of Fusiform Aneurysms," IEEE Transactions on Biomedical Engineering, vol. 54, No. 6, Jun. 2007m pp. 1157-1160.

James et al., "On imparting radiopacity to a poly(urethane urea)," Biomaterials, vol. 28, 2007, pp. 3182-3187.

Sang et al., "Radiopaque Iodinated Polyurethane for Embolic Agents," ACTA Polymerica Sinica, No. A1, 2014, pp. 31-39.

European Patent Office, Office Action dated Feb. 15, 2021 in European Patent Application No. 17876750.5 (4 pages).

Japanese Patent Office, Office Action dated Aug. 31, 2021 in Japanese Patent Application No. 2019-529556 (8 pages).

James et al., "On imparting radiopacity to a poly(urethane urea)", Biomaterials, vol. 28, Issue 21, 2007, pp. 3182-3187.

Heart's Section 4, 2009, vol. 41, No. 3, pp. 277-284.

Chinese Patent Office, Office Action dated Sep. 8, 2021 in Chinese Patent Application No. 201780074595.7 (37 pages).

Japanese Patent Office, Office Action dated Nov. 2, 2021 in Japanese Patent Application No. 2019-530119 (11 pages).

* cited by examiner

| Foam Property | Criteria | Acceptable | Ideal | Description |
|---|---|---|---|---|
| $T_g$ | °C | 30-50 | 20-80 | Demonstrate control over glass transition temperature |
| ATR-FTIR Spectra | $cm^{-1}$ | 500-850 | - | Aryl halide peaks to confirm covalent iodine attachment |
| Gel Fraction | % | 90 | 100 | Confirm a fully crosslinked polymer network |
| Foam Density | $g/cm^3$ | 0.040 | 0.025 | Low densities for embolic device design |
| Pore Size | μm | 400-600 | 300-400 | Small pores for embolic device prototyping |
| Tensile Strength | kPa | 80 | 120 | Stronger than nanoparticulate composite foams |
| Free Strain Recovery | % | 85 | 100 | Confirm shape memory capacity for volumetric occlusion |

FIGURE 5

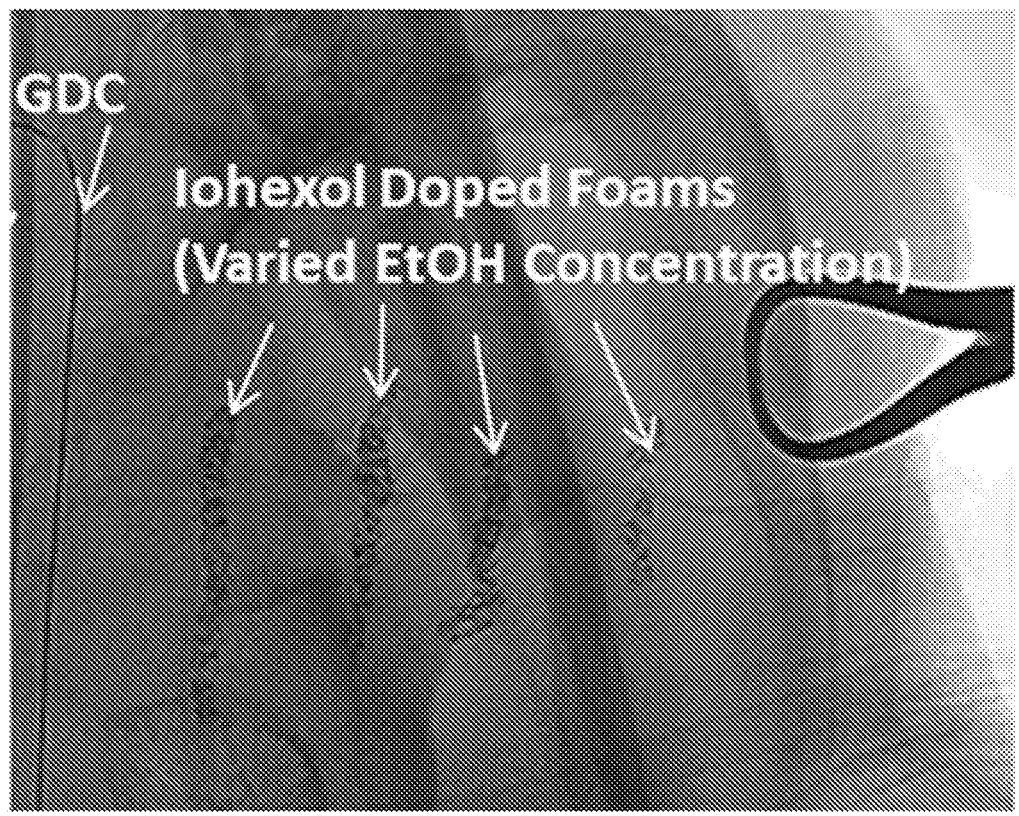

FIGURE 6

| | Foam ID | ATIPA% | MPD% | BEP% | HT% | NCO | Enovate | Scale |
|---|---|---|---|---|---|---|---|---|
| 1 | 0.0 ml Eno - 20AT | 20 | 40 | 20 | 20 | HDI | 0 ml | 8g |
| 2 | 0.5 ml Eno - 20AT | 20 | 40 | 20 | 20 | HDI | 0.5 ml | 8g |
| 3 | 1.0 ml Eno - 20AT | 20 | 40 | 20 | 20 | HDI | 1.0 ml | 8g |
| 4 | 1.5 ml Eno - 20AT | 20 | 40 | 20 | 20 | HDI | 1.5 ml | 8g |
| 5 | 2.0 ml Eno - 20AT | 20 | 40 | 20 | 20 | HDI | 2.0 ml | 8g |
| 6 | 10HT – 20AT | 20 | 50 | 20 | 10 | HDI | 1.5 ml | 8g |
| 7 | 20HT – 20AT | 20 | 40 | 20 | 20 | HDI | 1.5 ml | 8g |
| 8 | 30HT – 20AT | 20 | 30 | 20 | 30 | HDI | 1.5 ml | 8g |
| 9 | 40HT – 20AT | 20 | 20 | 20 | 40 | HDI | 1.5 ml | 8g |
| 10 | 0AT – 40HT | 0 | 40 | 20 | 40 | HDI | 1.5 ml | 8g |
| 11 | 10AT – 30HT | 10 | 40 | 20 | 30 | HDI | 2.0 ml | 8g |
| 12 | 20AT – 20HT | 20 | 40 | 20 | 20 | HDI | 1.5 ml | 8g |
| 13 | 30AT – 10HT* | 30 | 40 | 20 | 10 | HDI | 1.0 ml | 8g |
| 14 | 40AT – 0HT** | 40 | 40 | 20 | 0 | HDI | 1.0 ml | 8g |
| 15 | 20AT HDI | 20 | 40 | 20 | 20 | HDI | 1.5 ml | 8g |
| 16 | 20AT 50H/50TM | 20 | 40 | 20 | 20 | 50/50 | 1.5 ml | 8g |
| 17 | 20AT TM | 20 | 20 | 20 | 20 | TMHDI | 1.5 ml | 8g |
| 18 | 25AT 32g | 25 | 40 | 20 | 25 | HDI | 1.5 ml | 32g |
| 19 | 30AT 32g* | 30 | 40 | 20 | 20 | HDI | 1.5 ml | 32g |

FIGURE 9

|   | Composition | Density (g/cc) n=6 | Axial Pore Size (μm) n=10 | Transverse Pore Size (μm) n=10 | Dry Tg (°C) n=3 | Gel Fraction (%) n=5 |
|---|---|---|---|---|---|---|
| 1 | 0.0 ml Eno | 0.228±0.011 | 617±243 | 574±277 | 46.8±0.5 | - |
| 2 | 0.5 ml Eno | 0.149±0.013 | 1039±523 | 845±370 | 44±2.3 | - |
| 3 | 1.0 ml Eno | 0.075±0.001 | 856±321 | 974±502 | 47±0.4 | - |
| 4 | 1.5 ml Eno | 0.057±0.001 | 293±102 | 306±115 | 45±1.2 | - |
| 5 | 2.0 ml Eno | 0.045±0.004 | 401±158 | 332±126 | 44±0.7 | - |
| 6 | 10HT – 20AT | 0.051±0.001 | 402±191 | 311±112 | 41±1.0 | 94.5±2.5 |
| 7 | 20HT – 20AT | 0.057±0.001 | 293±102 | 306±115 | 45±1.2 | 95.1±0.6 |
| 8 | 30HT – 20AT | 0.051±0.001 | 384±152 | 364±190 | 53±2.1 | 96.9±0.5 |
| 9 | 40HT – 20AT | 0.044±0.001 | 372±161 | 434±243 | 58±2.1 | 99±0.4 |
| 10 | 0AT – 40HT | 0.078±0.003 | 231±120 | 233±123 | 38±0.1 | 95.8±3.9 |
| 11 | 10AT – 30HT | 0.062±0.009 | 1360±723 | 1130±399 | 37±0.4 | 98.7±0.7 |
| 12 | 20AT – 20HT | 0.057±0.001 | 293±102 | 306±115 | 45±1.2 | 95.1±0.6 |
| 13 | 30AT – 10HT | 0.041±0.005 | 558±346 | 579±238 | 52±1.5 | 96.4±0.6 |
| 15 | 100HDI | 0.057±0.001 | 293±102 | 306±115 | 45±1.2 | - |
| 16 | 50HDI/50TM | 0.049±0.002 | 517±314 | 482±287 | 50±0.5 | - |
| 17 | 100TM | 0.049±0.001 | 552±214 | 488±274 | 52±0.5 | - |
| 18 | 25AT 25HT 32g | 0.040±0.001 | 515±119 | 512±249 | Pending | - |
| 19 | 30AT 20HT 32g | 0.051±0.005 | 415±172 | 320±137 | Pending | - |

FIGURE 11

CHEMICALLY MODIFIED SHAPE MEMORY POLYMER EMBOLIC FOAMS WITH INCREASED X-RAY VISUALIZATION

CROSS-REFERENCE TO RELATED APPLICATION

This application claims priority to U.S. Provisional Patent Application No. 62/429,148 filed on Dec. 2, 2016 and entitled "CHEMICALLY MODIFIED SHAPE MEMORY POLYMER EMBOLIC FOAMS WITH INCREASED X-RAY VISUALIZATION", the content of which is hereby incorporated by reference.

STATEMENT OF FEDERALLY FUNDED RESEARCH

The U.S. Government may have certain rights in this invention pursuant to Contract No. NINDS U01-NS089692 awarded by NIH.

The U.S. Government may have certain rights in this invention pursuant to Contract No. GRFP 1252521 awarded by NSF.

TECHNICAL FIELD

Embodiments of the invention are in the field of shape memory polymer medical devices.

BACKGROUND

Approximately 3-4% of healthy, asymptomatic individuals have an unruptured cranial aneurysm. Upon aneurysm rupture, subarachnoid hemorrhage occurs, resulting in stroke and subsequent brain damage and possible death. With stroke ranking as the second highest cause of death worldwide, efficient embolization of cerebral aneurysms is required to prevent their rupture and reduce the morbidity and mortality of hemorrhagic stroke. Current treatments utilize minimally-invasive embolic coils to fill the aneurysm and cut off blood flow, but these devices are limited by their low volume occlusion and recanalization of the aneurysm. Thermally actuated shape memory polymer (SMP) embolic foams have shown promise as a superior option for treating cerebral aneurysms due to their high volumetric expansion capabilities and excellent biocompatibility.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIGS. 2(a) and 2(b) include different combinations of system materials for alternative embodiments.

FIG. 5: Foam acceptance criteria.

FIG. 6: 2.5 mm foam devices and a GDC platinum coil imaged through a porcine skull. Iohexol was solvent swelled into the foam with ethanol solutions at 10-40 wt %. Physical incorporation of iohexol produced unideal mechanical properties (but is included instead of or in addition to chemical inclusion in some embodiments).

FIG. 8(A)—Phase separated, cloudy foam with 20 eq % ATIPA synthesized with tertiary amine blowing catalyst. FIG. 8(B)—Optically clear foam with 30 eq % ATIPA synthesized without traditional foaming catalysts.

FIG. 9: Embodiments of ATIPA foam compositions. Monomers listed by mole percent.

FIG. 11: Physical and thermomechanical ATIPA foam properties of various embodiments.

FIG. 16(a)—representative stress strain curves for x-ray visible foams (ATIPA and Tungsten loaded and a non-visible control foam. FIG. 16(b)—mechanical property calculations from each curve.

DETAILED DESCRIPTION

Figure 1:
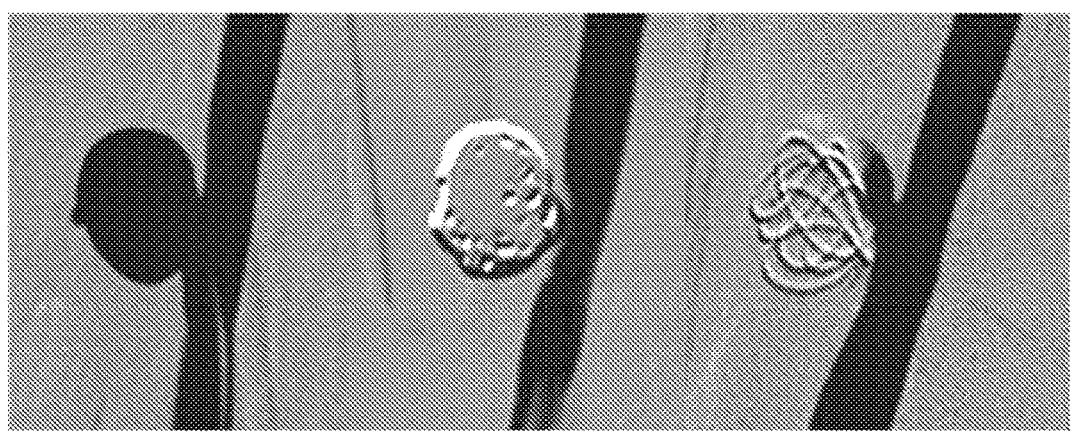
FIG. 1: Left—Untreated porcine side wall aneurysm model. Middle—Digital subtraction angiography of aneurysm model treated with bare platinum coils. Ingress of the contrast agent injection is masked by the 2D coil projection. Right—Angiography image of aneurysm treated with SMP foam-coated embolic coils. Ingress of the contrast injection into the aneurysm is prevented by a mass of embolic foam and thrombus.

"An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner.

To enable proper SMP-based device placement, Applicant determined the material must be visible using traditional fluoroscopic techniques. Without device visualization, the use of this highly valuable material system in cerebral aneurysm treatment will be limited.

Below various embodiments are addressed. Embodiments are first addressed in the section entitled "OVERVIEW OF AN EMBODIMENT". Embodiments are then further addressed in sections entitled "HIGH LEVEL DESCRIPTION OF EMBODIMENTS" and "MORE DETAILED DESCRIPTION OF EMBODIMENTS."

Overview of an Embodiment

Embodiments include x-ray visible SMP foam systems for endovascular embolization devices and other implantable tissue scaffolds. An embodiment includes a thermoset biomedical shape memory polyurethane foam system that incorporates contrast agents as monomers. Once implanted within the desired anatomy using fluoroscopic techniques, these foams expand and fill the anatomical volume to promote embolization and subsequent cellular infiltration and healing. Enabling x-ray visualization of the SMP allows physicians to see the true volumetric filling of the foam as it expands. This increases procedural safety by enabling proper device placement and reducing the risk of overpacking the anatomy.

Embodiments include foam-only endovascular embolization devices that do not require metal components such as platinum backbone coils for fluoroscopic visualization. This enables more foam to be incorporated into the device cross section for better volumetric filling when delivered through similar sized catheters. Embodiments also overcome limitations of current embolic foam devices by giving the clinician the ability to directly visualize actual device expansion and anatomical filling. The porous nature of the material creates favorable healing outcomes and durable occlusion.

X-ray visualization is facilitated by including angiographic contrast agents as monomers into the polymer synthesis to chemically incorporate radio-dense triiodobenzene motifs into the polymer network. These groups are visible under fluoroscopy due to 3 covalently bound iodine atoms.

Such embodiments allow for safer treatment of intracranial aneurysms with better clinical outcomes. However, embodiments are suitable for other endovascular occlusion applications as well (e.g., filling a left atrial appendage, abdominal aortic aneurysm occlusion, peripheral vessel occlusion, and more generally filling a void in anatomy and/or around an medical device).

When compared to particulate additives, the chemical approach of incorporating triiodobenzene monomers into the material during synthesis enables higher contrast loading percentages without affecting the mechanical integrity of the bulk material. This radiodense SMP material system can be utilized to create low density foams for embolic applications without the need for metal components such as platinum backbones or marker bands. This material system allows for entirely polymeric, biodurable, embolic devices used for a variety of applications, including cerebrovascular or peripheral embolization. Incorporating aromatic diisocyanates also creates a very rigid polymer system appropriate for bone tissue applications that require x-ray visibility. Degradable linkages such as ethers, esters, or tertiary amines are incorporated in some embodiments to create a biodegradable material formulation.

These materials can be fabricated by combining, for example, (a) combinations of 5-amino-2,4,6-triiodoisophthalic acid (ATIPA), diethylene glycol (DEG), triethylene glycol (TEG), 2-butyl-2-ethyl-propanediol (BEP), 3-methyl-pentanediol, butanetriol, and hexanetriol, with (b) a diisocyanate (e.g. hexamethylene diisocyanate (HDI) or trimethyl hexamethylene diisocyanate (TMHDI)). Alternative compositions incorporate (instead of ATIPA) other iodine containing monomers such as Iohexol, triiodophenol, or diatrizoic acid. Alternative compositions also incorporate other polyols such as glycerol, trimethylolpropane, pentaerythritol, pentanediol, 3-methyl-1,3,5-pentanetriol, and cyanuric acid. Alternative compositions can also include multifunctional crosslinkers with terminal hydroxyl, amine, or carboxylic acid endgroups, such as 1,3-Diamino-2-propanol, aspartic acid, 1,2-diaminopropane, 2,2-Dimethyl-1, 3-propanediamine, 1,8-Diaminooctane, 3-Amino-1,2-propanediol, or 2-Amino-2-methyl-1,3-propanediol.

ATIPA serves as the contrast agent and blowing agent in the foaming reaction in some embodiments. Foams are synthesized through the addition of surfactants, tin gelling catalysts, tertiary amine blowing catalysts, and physical blowing agents such as Enovate®. Nano or micro particulate additives including platinum, tungsten, or tantalum can be added to the material during synthesis to create a composite with additional x-ray attenuation.

After synthesis, the material is cut, cleaned, processed, and incorporated into a medical device.

High Level Description of Embodiments

A—Specific Aims

Embodiments include an x-ray visible SMP embolic foam material system for the treatment of cerebral aneurysms. An embodiment enables x-ray contrast through the incorporation of radiodense iodine atoms into the polymer network. This chemical approach to opacification expands the utility of SMP embolic foams by addressing the limitations of non-visible formulations. A triiodobenzene-containing contrast agent is incorporated as a monomer into the shape memory polyurethane backbone, resulting in a radiodense polyurethane-urea-amide. In addition to providing x-ray visibility, this contrast agent monomer serves as a blowing agent during foaming and a chemical crosslinking agent to provide shape memory.

An embodiment enables control over the amount of x-ray contrast, thermomechanical properties, and foam morphology. The degree of x-ray contrast is controlled through the amount of contrast agent monomer present in the synthesis. Thermo-mechanical properties are altered by varying diisocyanate and polyol ratios during polyurethane synthesis. Foam morphology, such as pore size and density, is tailored via changes in foam premix viscosity and by altering the amount of physical blowing agent, surfactants, and catalysts during synthesis. The ability to independently control these material properties increases the utility of x-ray visible embolic foams by opening avenues for device optimization to meet specific application needs.

The following topics address the utility of the material system:

Topic 1: Chemically and thermo-mechanically characterize x-ray visible SMP formulations with varying contrast agent, polyol, and diisocyanate monomer formulations.

Topic 2: Tune foaming parameters to achieve foam densities, mechanical properties, and volumetric recoveries appropriate for neurovascular embolization.

Topic 3: Verify fluoroscopic visibility of an embolic foam device prototype delivered into an anatomical aneurysm model.

B—Significance

The current gold standard for preventing hemorrhagic stroke involves treating cranial aneurysms with bare platinum coils (BPCs). BPCs have helped to reduce the annual number of hemorrhagic strokes in the United States to approximately 103,000, but this treatment still has clinical limitations. For instance, packing densities that are considered to be very high by clinical standards (30-35%) still do not cause complete embolization. Attempts to increase packing density with more coils can lead to over-packing and aneurysm rupture. Furthermore, embolizations that are initially effective have recanalization rates as high as 35% and 50% in large and giant aneurysms, respectively. BPCs are cost prohibitive when utilized to fill large aneurysms due to the number of required coils, procedure time, and complexity. Thus, efficacy and cost limitations of BPCs demand solutions for more efficient volumetric filling.

Hydrocoils have been developed to increase volumetric aneurysm filling for comparable coil lengths. After implantation, the hydrophilic coating on these coils swells with water to effectively increase the coil diameter. Hydrocoils can consistently achieve packing densities above 50%, and often achieve densities 3 times greater than BPCs on their own. Despite their increased packing densities, studies have shown no clear advantage of hydrocoils in terms of preventing aneurysm recurrence, making the additional cost associated with these hydrophilic coatings unwarranted.

Low density SMP embolic foams have been proposed as a solution to alleviate the numerous drawbacks associated with current embolization therapies. Low density SMP foams can be crimped to fractions of their expanded volume, allowing delivery through a micro-catheter. After implantation, a stimulus, such as heat, can restore the crimped foam to its original expanded geometry. The volumetric expansion capabilities and demonstrated biocompatibility of SMP foams make them a promising solution for providing better filling and improved healing of aneurysm lesions. Results demonstrate biocompatibility of SMP foams implanted in a porcine carotid aneurysm model. Pathology results show superior healing capabilities of polyurethane SMP foams compared to those of implanted BPCs. However, the current SMP formulation's lack of x-ray visibility can limit its effective delivery in a clinical setting.

Many medical applications for SMPs involve endovascular delivery while imaging with fluoroscopy. Fluoroscopic device visualization is essential for the proper and safe placement of the device into the aneurysm anatomy. In the case of cerebral aneurysm embolization, the lack of SMP x-ray contrast can be partially addressed by utilizing the SMPs as a coating over a radiodense BPC. FIG. 1 highlights a limitation to this approach. The left hand frame depicts the typical anatomy of a porcine sidewall aneurysm model. The middle frame shows digital subtraction angiography of an aneurysm treated with traditional BPCs, which depicts the dense 2D projection of the coil mass that clinicians use as the primary indicator of sufficient coiling. Although the aneurysm appears to be densely packed with coils, the average packing density of embolic coils ranges between 30-35%. The right hand frame shows an aneurysm treated with SMP foam-coated embolic coils. The aneurysm appears to be loosely-filled according to the radiographic projection, but the limited ingress of injected contrast agent proves that the interstitial spaces between the coils are filled with non-x-ray visible embolic foam and thrombus. Using injected contrast agent as the primary indicator of aneurysm embolization is a hurdle for clinical adoption of the device, as it deviates from the standard 2D radiographic projection technique. This procedural change could potentially lead to over-packing the aneurysm with foam coated coils. However, embodiments reduce the risk of these complications by giving clinicians a better visual for true volumetric occlusion.

C—Innovation

Embodiments include ultra-low density SMP foams with mass densities as low as 0.015 g cm-3 and high crosslink densities that facilitate 97% shape recovery. These properties collectively enable 70× foam volumetric expansion. Utilization of these low density SMP foams in conjunction with current coiling techniques can significantly reduce the number of coils necessary to fill an aneurysm to reduce procedure time and cost. Additionally, SMP foam expansion forces are significantly lower than those applied by BPCs, lowering the risk of aneurysm dissection during implantation. Similar to other coil-based embolization devices, the embolic foam occludes the aneurysm by disrupting blood flow and inducing clot formation within the foam.

Previously, SMP foam x-ray visibility has been increased through the incorporation of tungsten microparticles into the foam matrix. However, this approach results in composites with diminished toughness, which raises concerns over particulate generation in vivo and subsequent emboli in the blood stream. Furthermore, the degree of opacification achieved with microparticle incorporation is not sufficient for small diameter, low density devices, such as those used for neurovascular embolization. Radiopaque nanoparticulate additives were investigated to address decreases in material toughness by increasing dispersion within the matrix. Low concentrations of nanoparticulates improved mechanical strength and toughness, but increasing filler concentration to that needed for sufficient x-ray visualization also resulted in diminished mechanical properties. Thus, there is a need for improved SMP x-ray contrast without sacrificing mechanical integrity.

As an alternative to opaque SMP micro or nanocomposites, embodiments incorporate iodine motifs into the polymer matrix to increase x-ray visibility without affecting the bulk foam properties. When compared to particulate additives, this chemical approach of incorporating triiodobenzene monomers into the material during synthesis enables higher contrast loading percentages without affecting the mechanical integrity of the bulk material. This radiodense SMP material system provides embodiments that include low density foams for embolic applications without the need for metal components such as platinum backbones or marker bands. This material system allows for entirely (or almost entirely) polymeric, degradable, embolic devices used for a variety of applications, including cerebrovascular or peripheral embolization. While this work focuses on the incorporation of iodine into a specific SMP foam system, embodiments are applicable to a range of polymeric biomaterials to enable their imaging during implantation.

D—Approach

Figure 2A:
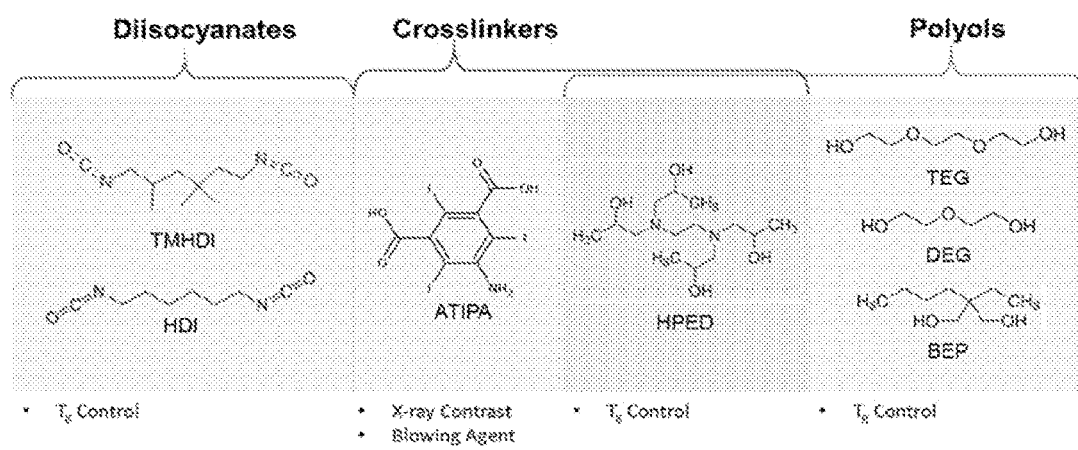
FIGS. 2(a) and 2(b): Material system monomers.
Figure 2B:
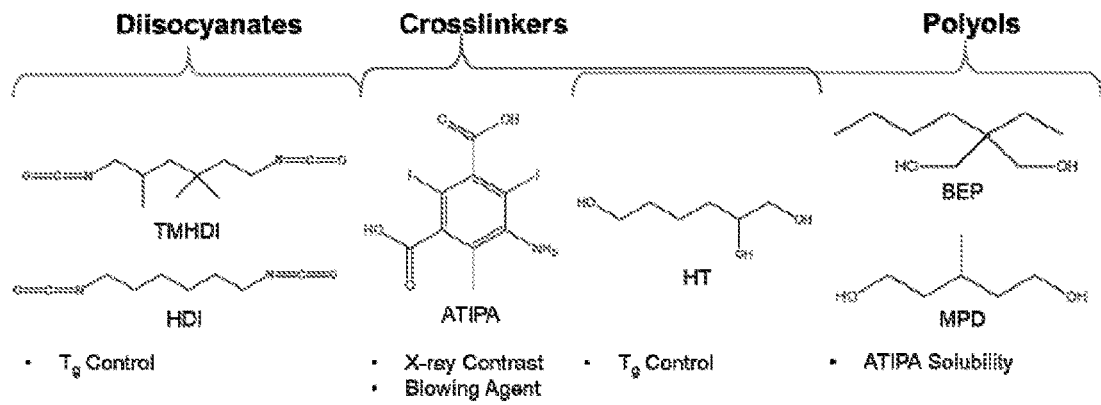

In an embodiment the contrast agent identified for use in SMP polymerization is 5-amino-2,4,6-triiodoisophthalic acid (ATIPA). As seen in FIGS. 2(a) and 2(b), the x-ray contrast of the ATIPA molecule is derived from the triiodobenzene motif, which incorporates three high-z iodine atoms. It is terminated with a primary aromatic amine and two carboxylic acids, giving it a functionality of three for crosslinking reactions with isocyanates. Further, the reaction between isocyanates and carboxylic acids yields an amide linkage and carbon dioxide, making ATIPA a chemical blowing agent during foam polymerization.

Also depicted in FIG. 2(a) are various diisocyanates and polyols selected for their favorable solubility and the ability to control both Tg and crosslink density of resulting SMP foams. The diisocyanates include hexamethylene diisocyanate (HDI) and trimethyl hexamethylene diisocyanate (TMHDI). Polyols include N,N,N',N' tetrakis hydroxypropyl ethylenediame (HPED), triethylene glycol (TEG), diethylene glycol (DEG), and 2-butyl-2-ethyl-1,3-propanediol (BEP). Polymer foams are synthesized with varied molar equivalent ratios of these constituents to quantify their effects on morphology and thermo-mechanical properties.

D.0—Data

Figure 3:
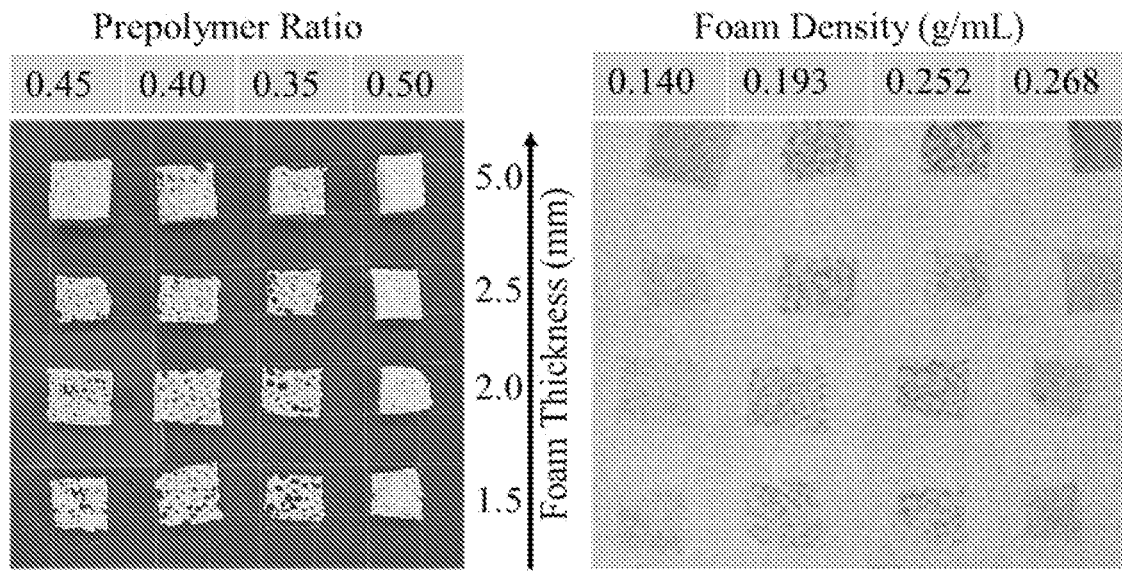
FIG. 3: Medium density foams made with HDI, 15/35/50 percent molar equivalents of ATIPA/BEP/DEG, respectively, and polyurethane foaming surfactants and catalysts. The X-ray image has no tissue analog to simulate imaging through the human skull.

A hurdle for polymerizing ATIPA is its limited solubility with other monomers, especially diisocyanates. A range of compositions have been successfully polymerized with ATIPA, DEG, BEP, and HDI to yield the polymeric foams shown in FIG. 3. These foams were blown with the ATIPA (15% molar equivalents) dicarboxylic acid reaction with diisocyanates and demonstrated x-ray contrast at 133 mg I/ml. Foam density and pore size were controlled by varying the premix viscosity with different percentages of prepolymer hydroxyl equivalent ratios.

D.1—Topic 1: Chemically and Thermo-Mechanically Characterize x-Ray Visible SMP Formulations with Varying Contrast Agent, Polyol, and Diisocyanate Monomer Formulations Embodiments include polymer samples with ATIPA varying from 20-30 mol % of the non-isocyanate components. Because this aim focuses on bulk material properties, samples are examined in their natural state, regardless of density. When using ATIPA as a monomer, 20-30 mol % provides approximately 175-275 mg I/ml. This iodine loading density is comparable to that of traditional angiographic contrast injection concentrations and provides sufficient material visualization at minimal path lengths.

Figure 4:
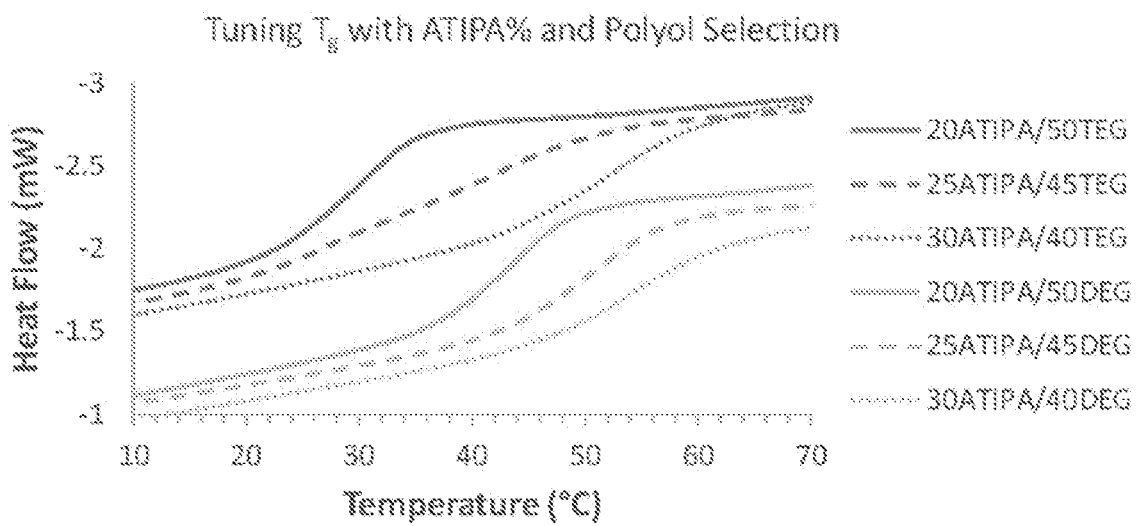
FIG. 4: Glass transition temperature tuned by varying ATIPA molar percentages 20-30%, and TEG/DEG percentages 40-50%. All compositions used 100% HDI, and the remaining polyol equivalents were BEP.

FIG. 4 shows differential scanning calorimetry (DSC) thermograms of two high density SMP foam systems that utilize different hydroxyl monomer compositions (40-50 mol % TEG or DEG) to tune Tg between 30 and 55° C. with ATIPA incorporated at varied concentrations. This data set shows that embodiments of the monomer combinations can be used to synthesize materials with transitions relevant for body temperature actuation. Further monomer combinations allow for tighter control of bulk thermomechanical properties, as determined by DSC. Embodiments are synthesized to bracket the ranges of molar equivalent ratios that are miscible. Other compositions include crosslinkers in addition to ATIPA for greater control over material properties including gel fraction and shape memory strain recovery.

FTIR spectra provide a chemical signature for each composition and verify the covalent incorporation of Iodine into the polymer network. Gel fraction analysis in tetrahydrofuran confirms sufficient crosslinking.

D.2—Topic 2: Tune Foaming Parameters to Achieve Foam Densities, Mechanical Properties, and Volumetric Recoveries Appropriate for Neurovascular Embolization Foam morphology is controlled by varying surfactant concentrations, catalyst concentrations (amine and tin), prepolymer hydroxyl ratios (viscosity), and physical blowing agent concentration (Enovate® 245fa). All catalysts and surfactants may be acquired through Air Products®. Temperature-dependent premix viscosity profiles may be obtained using a cone and plate viscometer. Scanning electron microscopy may quantify pore size and morphology of finished foams. Density may be measured by gravimetric analysis of uniform (1 $cm^3$) material blocks. Density and pore size success criteria may be based on specifications for a prototype neurovascular embolization device.

Foam samples may be $CO^2$ laser cut into dog bones for uniaxial tensile testing. Ultimate tensile strength, strain to failure, and toughness may be used to determine the functional relationships between foam morphology, composition, and mechanical integrity. A minimum tensile strength threshold (in some embodiments) of 80 kPa is based on the strength of SMP composites opacified with 7 volume percent nanoparticulate tungsten.

To determine the shape memory capacity of each formulation, cyclic free strain recovery and cyclic constrained recovery experiments may be conducted in compression on a TA Instruments Q800 Dynamic Mechanical Analyzer®. These experiments may quantify bulk thermo-mechanical properties including glassy modulus, rubbery modulus, and glass transition temperature. They may also quantify the shape fixity, recovery force, and strain recovery for each SMP foam composition. Compositions with higher ATIPA and HPED concentrations exhibit higher shape memory strain recovery due to higher crosslinking density. FIG. 5 summarizes all material characterization techniques for aims 1-2 and acceptance criteria used to select formulations for device prototyping.

D.3—Topic 3: Verify Fluoroscopic Visibility of an Embolic Foam Device Prototype Delivered into an Anatomical Aneurysm Model Embodiments may be delivered through a 0.021" ID microcatheter (thus embodiments have a crimped outer diameter that is less than the microcatheter's ID). The devices may be delivered under fluoroscopic visualization into an aneurysm phantom with simulated physiologic flow at body temperature. Competitive 360° GDC-10® bare platinum embolization coils may also be delivered into a phantom for comparison. All delivery procedures may be imaged through a ½" aluminum plate to simulate the opacity of the human skull. Devices may also be placed into a planar fixture and imaged through hard and soft porcine tissue. FIG. 6 shows an example fixture of 2.5 mm foams with iohexol physically incorporated into the material via solvent swelling.

D.4—Alternative Embodiments

Figure 7:
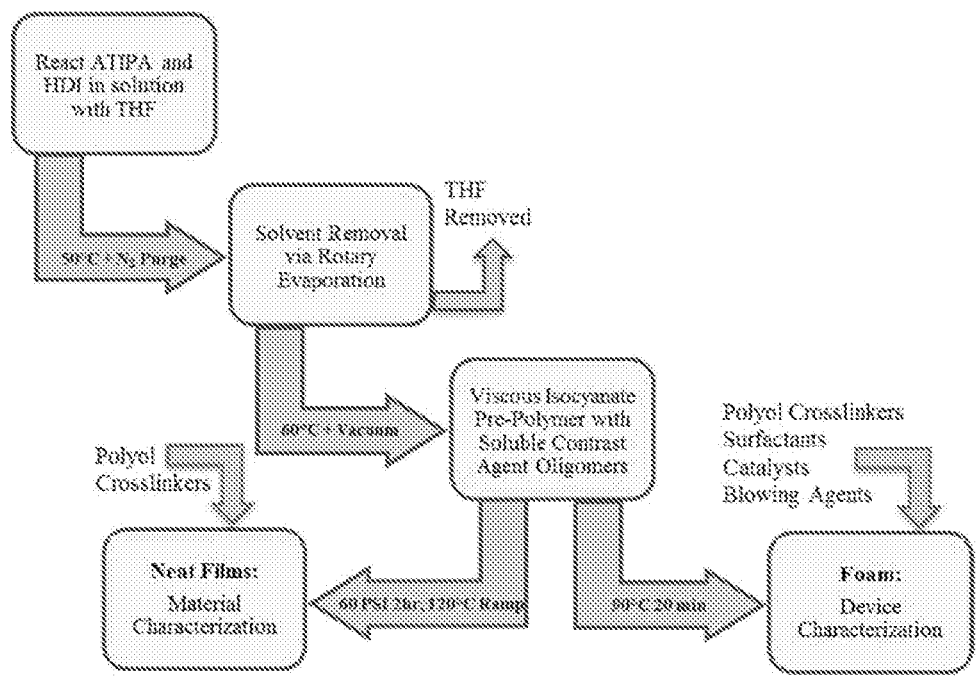
FIG. 7: Alternative solvent based synthetic strategy to alleviate potential monomer miscibility concerns.

Some embodiments include a solvent-based synthetic approach to improve on bulk curing approach (instead of or in addition to the above mentioned covalent bonded iodine based monomer). The contrast agent is designed to dissolve in highly polar solvents, such as water and alcohols, that are not suitable for use in polyurethane synthesis. However, ATIPA is soluble in tetrahydrofuran (THF), dimethyl formamide (DMF), and dimethyl sulfoxide (DMSO). FIG. 7 summarizes an alternative synthetic strategy for incorporating the solid ATIPA monomer into a polyurethane SMP foam. First, the contrast agent is pre-polymerized with an excess of HDI in an anhydrous THF solution. This initial pre-polymerization eliminates solubility issues and facilitates the use of numerous polyols for manipulating Tg and crosslink density in the final material. Additionally, this step effectively removes $CO^2$ generation from the foaming step to enable foaming control independent of ATIPA content. After pre-polymerization, the THF is removed from the oligomer solution using rotary evaporation. In some embodiments the pre-polymer solution is mixed with stoichiometric equivalents of polyols and cured into neat films. In embodiments polymer foams may be synthesized by combining the pre-polymer solution with polyol crosslinkers, surfactants, polyurethane catalysts, and physical blowing agents. Amide catalysts for the carboxylic acid reactions may be used in some embodiments for further foam optimization.

As an alternative to ATIPA, Iohexol is a FDA-approved angiography contrast agent. This molecule is water soluble, generally biocompatible, and cleared by the kidneys. Iohexol is terminated by six hydroxyl functionalities, which facilitate water solubility and can serve as reactive sites for polymerization. Iohexol is soluble in dimethyl formamide (DMF) and dimethyl sulfoxide (DMSO).

These were chosen as alternative synthetic strategies due to additional fabrication complexity and concerns with residual solvent. The neat polymer films may be chemically characterized using Fourier transform infrared spectroscopy (FTIR) and gel fraction analysis. Each material composition may also be thermo-mechanically tested using tensile testing, dynamic mechanical analysis (DMA), and differential scanning calorimetry (DSC). Compositions may be down-selected for foaming based on physiologic glass transition temperatures (DSC), maximized toughness (tensile testing), and rubbery modulus (DMA), similar to the proposed specific aims.

Thus, embodiments provide an x-ray visible SMP material system with flexible structure-to-property relationships that can be tuned for characterization of a neurovascular embolization device. Control over key material parameters enables embodiments.

More Detailed Description of Embodiments

Applicant fabricated ultra-low density SMP foams with mass densities as low as 0.015 g cm-3 and high crosslink densities that facilitate 97% shape recovery. These properties collectively enable 70× foam volumetric expansion. Utilization of these low density SMP foams in conjunction with current coiling techniques can significantly reduce the number of coils necessary to fill an aneurysm to reduce procedure time and cost. Additionally, SMP foam expansion forces are significantly lower than those applied by BPCs, lowering the risk of aneurysm dissection during implantation. Similar to other coil-based embolization devices, the embolic foam occludes the aneurysm by disrupting blood flow and inducing clot formation within the foam.

Many medical applications for SMPs involve endovascular delivery while imaging with fluoroscopy. Fluoroscopic device visualization is essential for the proper and safe placement of the device into the aneurysm anatomy. In the case of cerebral aneurysm embolization, the lack of SMP x-ray contrast can be partially addressed by utilizing the SMPs as a coating over a radiodense BPC. FIG. 1 highlights a limitation to this approach. The left hand frame depicts the typical anatomy of a porcine sidewall aneurysm model. The middle frame shows digital subtraction angiography of an aneurysm treated with traditional BPCs, which depicts the dense 2D projection of the coil mass that clinicians use as the primary indicator of sufficient coiling. Although the aneurysm appears to be densely packed with coils, the average packing density of embolic coils ranges between 30-35%. The right hand frame shows an aneurysm treated with SMP foam-coated embolic coils. The aneurysm appears to be loosely-filled according to the radiographic projection, but the limited ingress of injected contrast agent proves that the interstitial spaces between the coils are filled with non-x-ray visible embolic foam and thrombus. Using injected contrast agent as the primary indicator of aneurysm embolization is a hurdle for clinical adoption of the device, as it deviates from the standard 2D radiographic projection technique. This procedural change could potentially lead to over-packing the aneurysm with foam coated coils. The proposed x-ray visible SMP formulation is intended to reduce the risk of these complications by giving clinicians a better visual for true volumetric occlusion Previously, SMP foam x-ray visibility has been increased through the incorporation of tungsten microparticles into the foam matrix. However, this approach results in composites with diminished toughness, which raises concerns over particulate generation in vivo and subsequent emboli in the blood stream. Furthermore, the degree of opacification achieved with microparticle incorporation is not sufficient for small diameter, low density devices, such as those used for neurovascular embolization. Radiopaque nanoparticulate additives were investigated to address decreases in material toughness by increasing dispersion within the matrix. Low concentrations of nanoparticulates improved mechanical strength and toughness, but increasing filler concentration to that needed for sufficient x-ray visualization also resulted in diminished mechanical properties. Thus, there is a need for improved SMP x-ray contrast without sacrificing mechanical integrity.

In particular, bulk material addition of tungsten microparticles to SMP embolic foams has not been successful for inducing sufficient x-ray contrast for neurovascular applications. Further, increasing the particulate loading percentage for improved material contrast results in undesirable mechanical performance, including a reduction in fracture toughness and increased particulate generation.

As an alternative to opaque SMP micro or nanocomposites, an embodiment incorporates iodine motifs into the polymer matrix to increase x-ray visibility without affecting the bulk foam properties.

When compared to particulate additives, the chemical approach of incorporating triiodobenzene monomers into the material during synthesis enables higher contrast loading percentages without affecting the mechanical integrity of the bulk material. This radiodense SMP material system provides embodiments that include low density foams for embolic applications without the need for metal components such as platinum backbones or marker bands. This material system provides embodiments with entirely (or almost entirely) polymeric, degradable, embolic devices used for a variety of applications, including cerebrovascular or peripheral embolization. While this work focuses on the incorporation of iodine into a specific SMP foam system, embodiments are applicable to a range of polymeric biomaterials to enable their imaging during implantation.

FIG. 6 shows results for combining radiographic contrast agents with shape memory polymer foam for x-ray visualization. These 2.5 mm diameter foam cylinders were solvent swelled with solutions of iohexol dissolved in ethanol and vacuum dried. The expanded foams were imaged through a porcine skull with traditional fluoroscopy. These composites showed comparable visualization to a commercial GDC10 embolic coil. Although visible, physical incorporation of iohexol produced undesirable mechanical properties comparable to a ceramic material, further motivating chemical incorporation (but are still included instead of or in addition to chemically incorporated systems in some embodiments).

FIG. 2(a) depicts the monomers selected to investigate an x-ray visible SMP system. Aliphatic isocyanates were chosen for a polyurethane composition based on biocompatibility in embolic applications. Changing the molar ratio of HDI and TMHDI were used to control Tg and bulk material hydrophobicity for tailored material expansion rate.

In an embodiment the contrast agent monomer is 5-amino-2,4,6-triiodoisophthalic acid (ATIPA). The x-ray contrast of the ATIPA molecule is derived from the triiodobenzene motif, which incorporates three high-z iodine atoms. It is terminated with a primary aromatic amine and two carboxylic acids, giving it a functionality of three for crosslinking reactions with isocyanates. Further, the reaction between isocyanates and carboxylic acids yields an amide linkage and carbon dioxide, making ATIPA a chemical blowing agent during foam polymerization.

Solubility was a significant barrier for the development of this system. ATIPA is a hydrophilic solid monomer with zero solubility in isocyanates. ATIPA is soluble in tetrahydrofuran and dimethylsulfoxide, but a solvent free synthetic procedure is preferable to mitigate organic contaminants in end use medical products (at least in some embodiments). The proposed polyols 2-butyl-2-ethyl propanediol (BEP), 3-methyl-1,5-pentanediol (MPD), diethylene glycol (DEG), triethylene glycol (TEG), 1,2,4-butane triol (BT) and 1,2,6-Hexane triol (HT) were selected based on favorable ATIPA solubility and Tg control in the final material.

Figure 8:
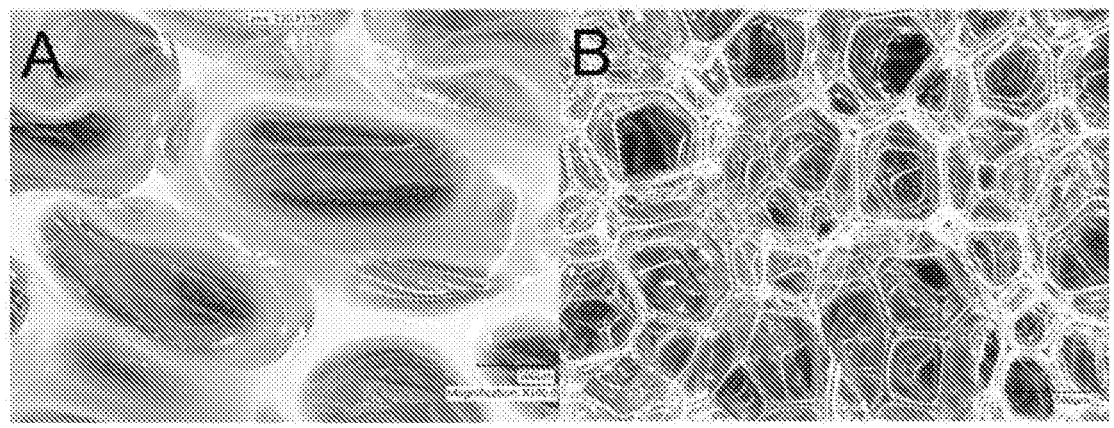
FIG. 8.

FIG. 8 depicts an additional solubility hurdle with these materials. Although the premix resins demonstrated favorable solubility, the final material exhibited considerable phase separation. ATIPA precipitation was predominantly seen during the addition of tertiary amine blowing catalysts. This type of precipitation was also seen with early material development with the polyol crosslinking monomers HPED and TEA. It was concluded that tertiary amines cause ATIPA precipitation out of solution and should be avoided in some embodiments but not in others. Even without catalysts, the reactivity of ATIPA does not lead to significant adverse effects when foaming the material.

Discussion below focuses on the optimization of a system utilizing HDI, TMHDI, ATIPA, BEP, MPD, and HT. MPD was proposed to replace TEG and DEG to mitigate the risk of degradation product biocompatibility by creating a theoretically more biodurable aliphatic system that does not incorporate ether linkages that are susceptible to oxidative degradation.

Materials and Methods

Foam Synthesis

FIG. 9 summarizes embodiments of foam compositions that were synthesized. For the A side of the polyurethane synthesis, the reactive hydroxyl, amine, and carboxylic acid functional groups are considered for the eq % calculations. A 2% molar excess of isocyanate was added to each foam synthesis to account for ambient moisture contamination during foam mixing. HDI, TMHDI, BEP, MPD, ATIPA, and HT were used as received from VWR Scientific and Sigma Aldrich.

Figure 10:
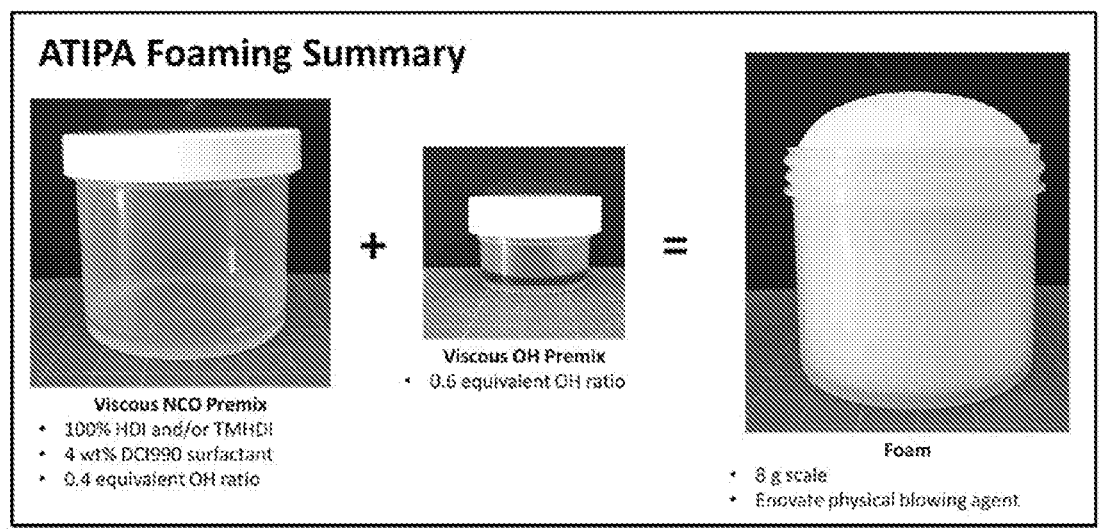
FIG. 10: ATIPA foaming process summary in an embodiment.

FIG. 10 provides an overview of the ATIPA foaming protocol. In summary, hydroxyl (OH) premixes were prepared 1 day prior to foaming by combining a 0.6 equivalent ratio of non-isocyanate monomers (ATIPA, BEP, MPD, HT) to a 15 ml polypropylene flactek mixing cup. The contents were mixed for 30 seconds at 3400 rpm in a FlacTek® high speed shear mixer, heated at 50° C. for 1 hour, mixed again for 30 seconds at 3400 rpm, and heated overnight at 50° C. For the 30 and 40 eq % ATIPA composition, 5 wt % and 8 wt % anhydrous THF were added to the OH premix to achieve complete solubility.

Viscous isocyanate (NCO) premixes were prepared in a desiccated glovebox by adding 0.4 molar ratio of reactive polyol equivalents to the entirety of diisocyanate equivalents in a 150 ml polypropylene FlacTek® mixing cup. Contents were mixed at 3400 rpm for ten minutes until a single phase was achieved. This premix was shaken at 1 rpm at room temperature for 2-5 hours until the mixture achieved a room temperature viscosity comparable to honey. For the OAT composition, 0.04 g of Air Products® T131 gelling catalyst and 0.08 g of Air Products® BL22 blowing catalyst were added to increase curing time during foaming.

To stabilize the foam during blowing, 4 wt % DCI990 surfactant was added to the NCO premix and mixed for 30 seconds. The OH premix was added to the NCO premix and mixed for 30 seconds. 1-2 ml of Enovate® was immediately added to the reactive resin and mixed for 30 seconds. The reaction was immediately moved to a 90° C. oven for a 20 minute cure. After curing, the foam skin was removed with a razor, and the foam was post cured at 50° C. for 12 hours. Post cured foams were cubed and stored in desiccated polypropylene bags.

Physical Characterization

Pore sizes were determined from light microscopy images acquired at 50× and 100× magnification using a Keyence® VHX-5000 metrology system with a variable illumination adapter. Foam samples were cut into 2-4 mm slices in the axial and transverse planes. Ten pore diameter measurements were taken for each foam image.

Six cubes measuring approximately 1 cm3 were taken from each composition for density measurement. Density was calculated at the sample mass divided by the product of the length, width, and height of the sample.

Fluoroscopy

Foam samples were prepared for x-ray imaging by cutting 1 cm×1 cm samples into 8, 4, 2, and 1 mm thick slices and adhering them to a polypropylene sheet. Each foam array included a platinum embolic coil as a radiographic standard. Peripheral occlusion prototypes were prepared by cutting foams into 8 mm diameter cylinders and axially threading them over a 0.006" stainless steel wire. One prototype was imaged in the expanded state while the other was axially crimped using a machine solutions SC250 heated stent crimper. The sample was equilibrated at 100° C. in the crimping bore for 15 minutes, radially compressed, and constrained while cooling to ambient temperature. Neurovascular prototypes 2 mm in diameter and without a backbone wire were also prepared and axially crimped. Angiography and fluoroscopy images were acquired using a Philips® Allura Xper FD20 x-ray system.

DSC

Dry Tg was determined using a TA Q200® Differential Scanning calorimeter on 5-10 mg foam samples in a vented aluminum pan. The samples were equilibrated at −40° C. for 5 minutes, then heated to 120° C., cooled to −40° C., and reheated to 120° C. at temperature ramps of 10° C./min. Tg was calculated at the inflection point of the second heating curve.

Example 24a recites a Tg that is calculated using this process described in the paragraph immediately above (i.e., Tg as recited in the claims is to be calculated using the above test regarding time, temperature, process, and inflection point of the second heating curve).

Wet Tg foam samples were immersed in 50° C. water for 30 minutes to achieve moisture plasticization. Moisture was removed by compressing the foam between tissue paper at 2 tons for 30 seconds using a Carver® laboratory press. 5-10 mg foam samples were added to an aluminum pan and hermetically sealed. Samples were cooled to −40° C., equilibrated for 5 minutes, and heated to 100° C. at 10° C./min. Wet Tg was calculated from the heating curve inflection point.

DMA

Dynamic mechanical analysis was conducted using a TA Q800®. Foam cylinders were prepared with an 8 mm biopsy punch and cut to approximately 5 mm in length using a razor. Samples were equilibrated to 0° C. for 5 minutes and heated to 120° C. at 3° C./min while undergoing 40 μm deformation at 1 Hz.

Unconstrained Expansion

Foams with varying HT content were cut into 2 mm diameter cylinders and axially threaded over 0.006" stainless steel wires. Samples were radially compressed using a Machine Solutions® SC250 heated stent crimper. Crimped samples were allowed to relax 24 hours before being expanded in a 37° C. water bath. Samples were imaged at 5 minute intervals for a total of 45 minutes. Five diameter measurements were taken along the length of the expanding foam using ImageJ® software.

ATR FTIR

ATR FTIR spectra were obtained using a Bruker ALPHA Infrared Spectrometer® with a diamond ATR® crystal. Data analysis was conducted using Bruker OPUS Spectroscopy Software®.

Tensile Testing

Dry foam samples were prepared using an ASTM Type IV dog bone punch.

Uniaxial tensile tests were conducted at room temperature using an Insight 30 Material Tester® MTS Systems Corporation, Eden Prairie, Minn.) with a constant strain rate of 50 mm/min. Ultimate tensile strength (kPa), strain at break (%), and elastic modulus (kPa) were calculated from the stress-strain curve of each sample.

Gel Fraction

Foam samples measuring approximately 1 cubic centimeter were cleaned to remove residual surfactant using three 30 minute sonication intervals in isopropyl alcohol at a 20:1 dilution ratio. The samples were dried under vacuum at 100° C. for 12 hours. Dried foam samples were massed and added to 20 ml vials filled to the shoulder with THF and heated at 50° C. with 1 Hz oscillation for 48 hours. The THF was removed and samples were dried under vacuum at 60° C. for 24 hours. Gel fraction is reported as the final sample mass divided by the original sample mass.

Results and Discussion

For compositions 1-5 of FIG. 11 with varying volumes of Enovate®, there is an obvious trend of decreasing material density with increasing volume of physical blowing agent. Although there is a statistically significant difference in the dry Tg values (1 way ANOVA, α=0.05), this variation is not expected to significantly affect device design criteria. The relationship between material density and pore morphology is better illustrated in light microscopy images presented in the next section.

Compositions 6-9 with varying HT content have comparable density and consistent average pore diameters in the 300-400 μm range. There is a statistically significant difference between the dry Tg's for each composition (1 way ANOVA, α=0.01). Increasing HT content increases the material crosslink density. Decreasing the molecular weight between crosslinks leads to higher network rigidity and higher glass transition temperatures. These compositions demonstrated that HT composition is an effective way to control Tg at fixed contrast agent loading (20% ATIPA) and foam density.

The ATIPA content was varied for compositions 10-13. HT content was also changed to maintain a consistent theoretical crosslink density. These foams demonstrated decreased bulk density with increasing ATIPA content. This result is expected due to the blowing reaction generated by the two carboxylic acid groups present on the ATIPA monomer. Dry Tg increases with increasing ATIPA content. Although the theoretical crosslink density for these compositions is constant, the aromatic structure of ATIPA is more rigid than the aliphatic HT monomer, increasing network rigidity and glass transition temperatures.

Compositions 15-17 all have 20 eq % ATIPA with varying isocyanate content. Changing the isocyanate composition demonstrated a less significant effect on Tg than altered HT content. Although foams with increased TMHDI content were successfully fabricated, they were qualitatively brittle compared to HDI foams and were not selected for further device optimization, however are appropriate in some embodiments.

Average gel fractions for selected compositions ranged between 94.5-99.0%. These values are comparable to those reported in previous non visible SMP foam formulations. High gel fractions reduce the risk for complications related to leachable chemicals exited a permanently implanted biomaterial. If necessary, this risk could be further mitigated with a more rigorous foam cleaning protocol to remove any potential unreacted leachables prior to device implantation.

After characterizing foams 1-17, compositions 18 and 19 were fabricated at 4× scale for tensile testing and neurovascular prototype fabrication. These compositions incorporated chemistry changes to achieve desirable morphology and thermomechanical properties.

Light Microscopy

Figure 12:
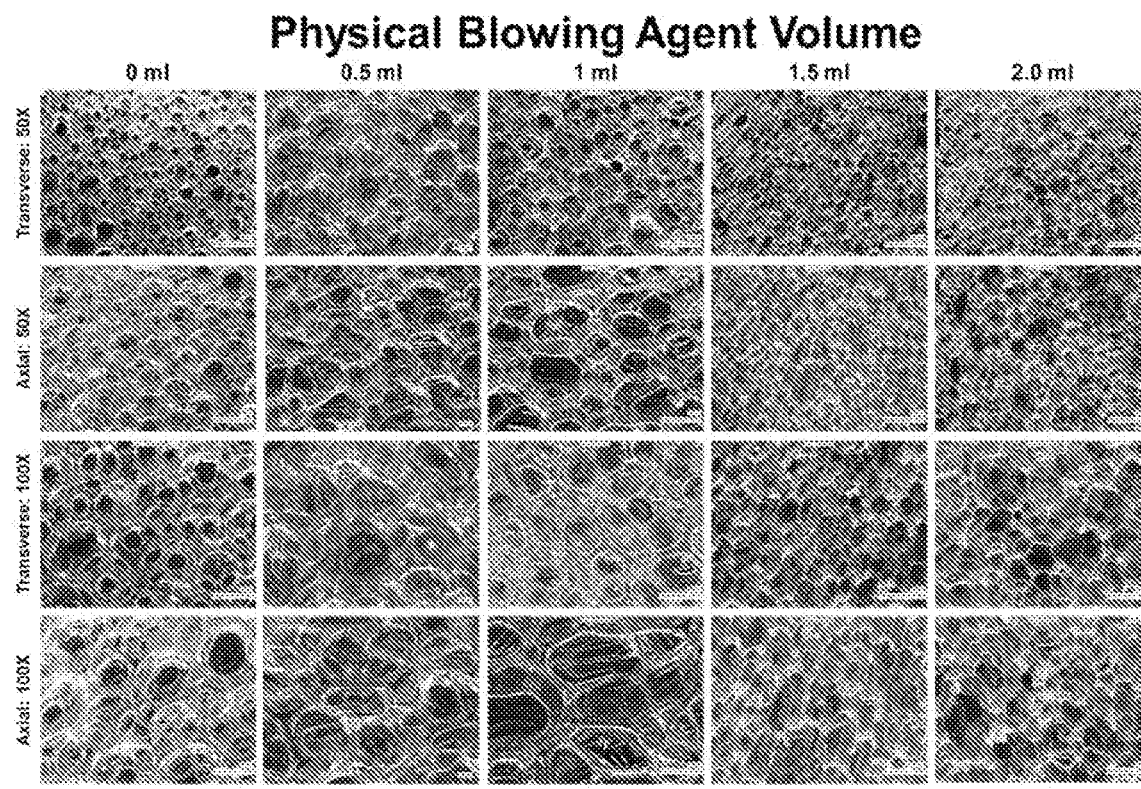
FIG. 12: Microscopy images at 50× and 100× magnification for an ATIPA foam series varying physical blowing agent (Enovate®) volume.

FIG. 12 illustrates the impact that increasing blowing agent has on foam morphology. The "0 ml" composition that uses no physical blowing agent still has porosity due to the ATIPA blowing reaction. Although these pores are comparable in size to the 0.5 ml and 1.0 ml foams, the strut morphology explains the significant difference in bulk material density. Similarly, the smaller pores in the 1.5 ml and 2.0 ml foam yield the least dense materials due to thin strut structures.

Figure 13:
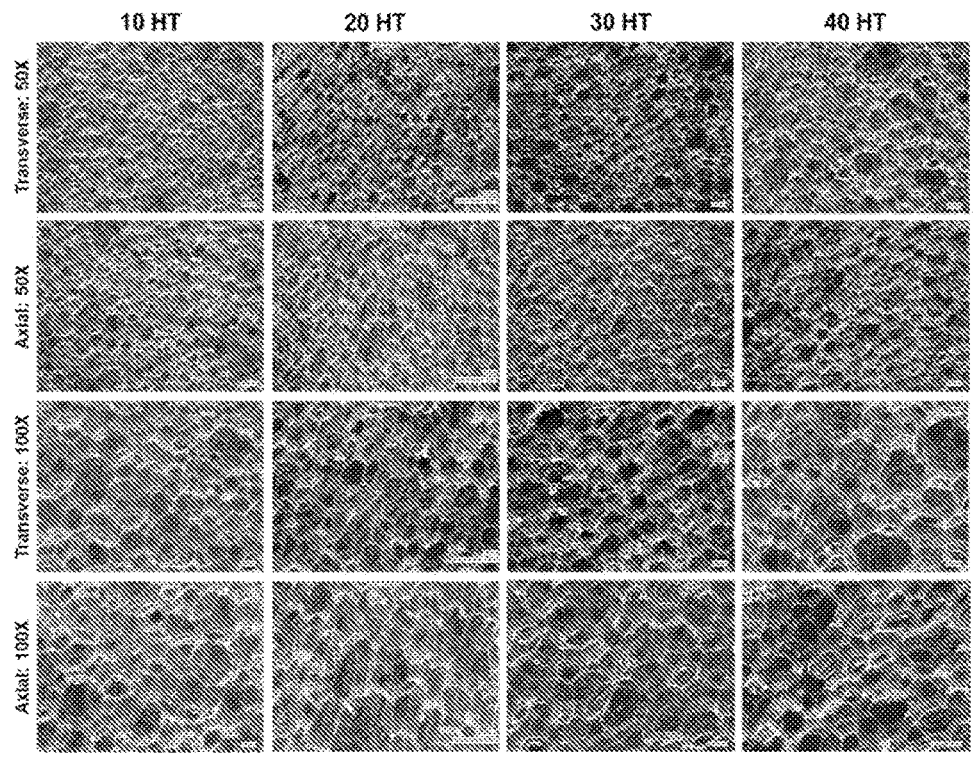
FIG. 13: Microscopy images at 50× and 100× magnification for foams with 20 eq % ATIPA and varying Hexanetriol composition.

FIG. 13 depicts foams with varying HT composition with comparable pore size, density, and strut morphology. It is important to note that composition, and subsequent thermomechanical properties can be altered independent of foam morphology to enable material optimization towards target medical device applications. Using both chemical ATIPA blowing and physical blowing enable morphology control independent of composition.

Figure 14:
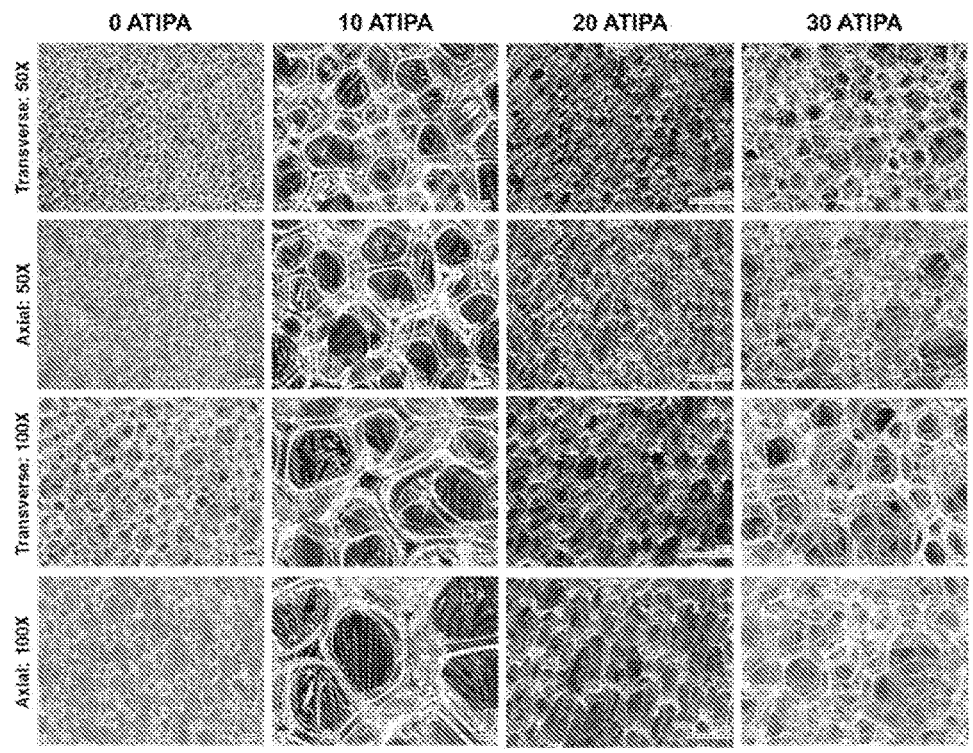
FIG. 14: Microscopy images at 50× and 100× magnification for foams with varying ATIPA content.

The foams in FIG. 14 have significant differences in pore morphology because the foaming parameters were not altered to compensate for changes in premix viscosity due to changing ATIPA content. However, this series demonstrated miscibility up to 30 eq % ATIPA. It is important to note that the 30 eq % ATIPA composition required 5 wt % of anhydrous THF during synthesis to prevent ATIPA precipitation.

Figure 15:
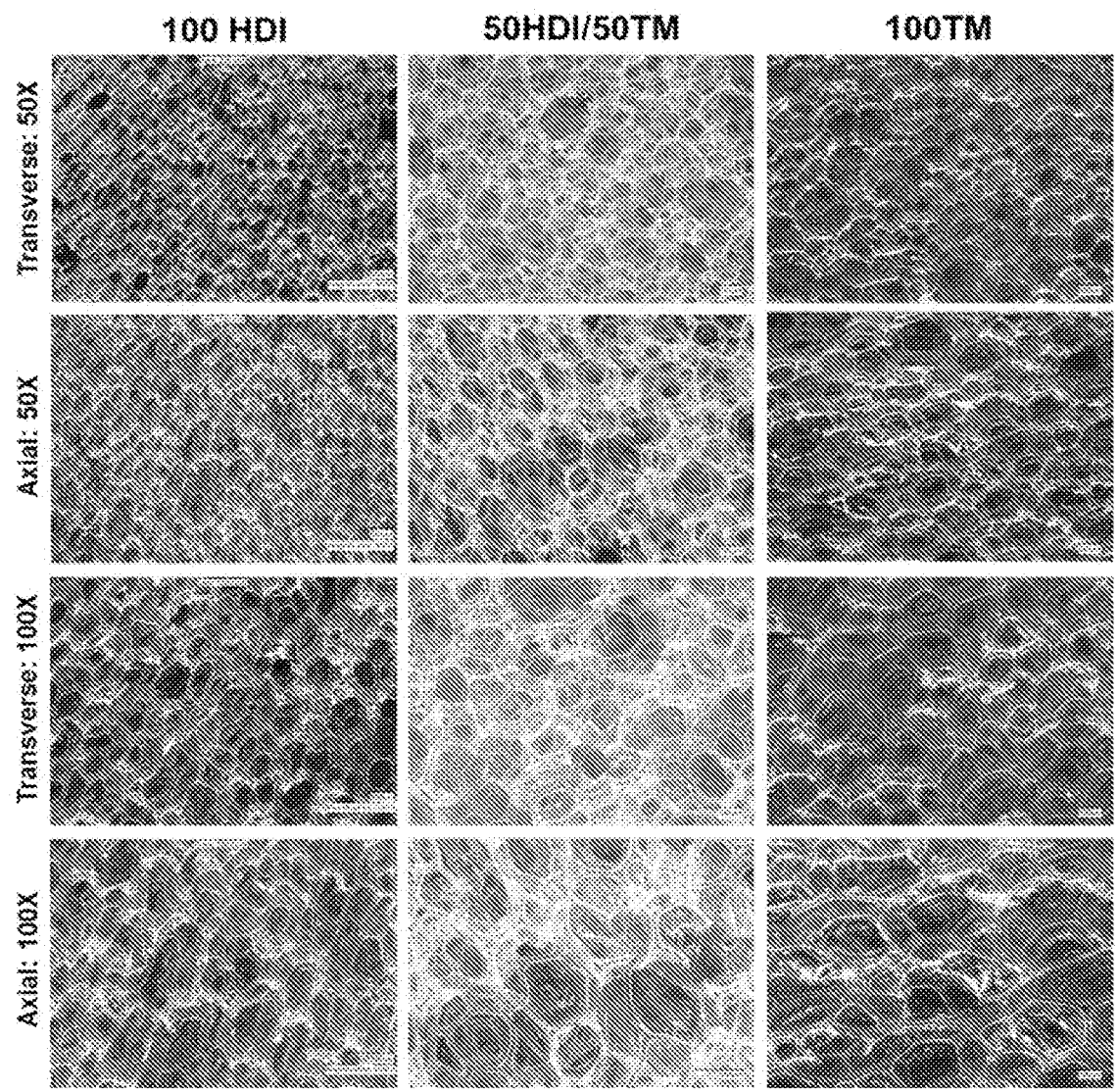
FIG. 15: Microscopy images at 50× magnification for ATIPA foam series varying isocyanate composition.

FIG. 15 details foams with varying isocyanate content. All foams demonstrate qualitative optical clarity. This promising monomer miscibility makes isocyanate composition a variable to control bulk thermomechanical properties and hydrophobicity for tailored material performance.

Tensile Testing

Figure 16:
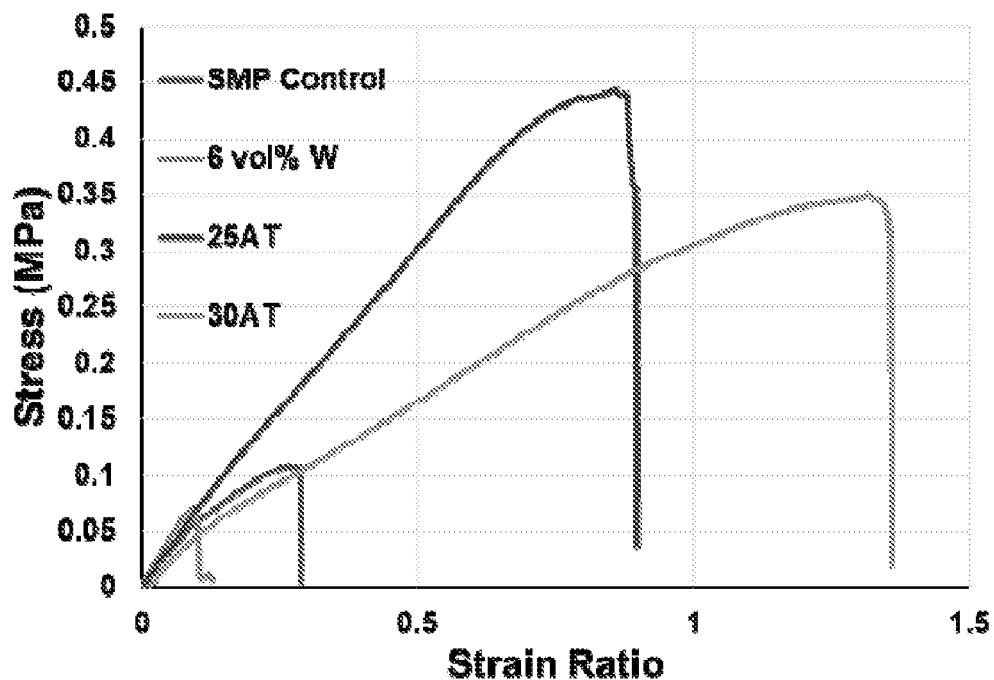
FIGS. 16(a) and 16(b)

FIG. 16 shows representative stress vs strain curves and affiliated calculations for a conventional SMP foam, a tungsten loaded SMP composite, a 25 eq % ATIPA foam, and a 30 eq % ATIPA foam (compositions 18 and 19).

These new ATIPA foam compositions achieve unprecedented material properties for low density SMP foams. The increased material strength (peak stress) is attributed to the aromatic structure of the ATIPA monomer. Applicant traditionally avoided aromatic polyurethane monomers, such as Toluene Diisocyanate, due to concerns with the biocompatibility of aromatic diamines in degradation products. However, aromatic compounds traditionally display higher strength when compared to their aliphatic counterparts. Although this polymer system was designed to be biodurable with minimal sites for oxidative or hydrolytic degradation, the biocompatibility of aromatic degradation products is satisfactory in some embodiments.

Increases in ductility (strain at break) are attributed to a decrease in crosslink density compared to the non-visible control SMP foam. The foams traditionally used by Applicant used polyols with functionalities of 3 (TEA) or 4 (HPED). These crosslinking sites are bridged by short diisocyanate segments (TMHDI or HDI) to create a highly crosslinked material. This crosslink density affords excellent shape memory, but at the relative expense of overall toughness. Applicant determined this is not a problem in a neat foam, but becomes problematic with Tungsten loaded composites that introduce stress concentrations in the strut cross section. Alternatively, the proposed ATIPA compositions employ the aliphatic diols MPD and BEP to increase the molecular weight between crosslinks for increased ductility. The rigidity of ATIPA enables this chain extension while keeping the transition temperature of the overall material within a functional biomedical range (40-60° C.).

The combined increases in ductility and strength contribute to significant increases in tensile toughness. Compared to non-visible foams, 25AT and 30AT compositions are over 11 and 14 times tougher, respectively. Compared to 6 vol % Tungsten nanoparticle foams, 25AT and 30AT foams are 46 and 57 times tougher, respectively. This dramatic increase in toughness significantly lowers the risk of undesired embolic particles detaching from the foam and flowing downstream from the target therapeutic region. Alternatively, foaming parameters could be optimized to introduce cell openers to create open porosity in the native foam.

X-Ray Imaging

Figure 17:
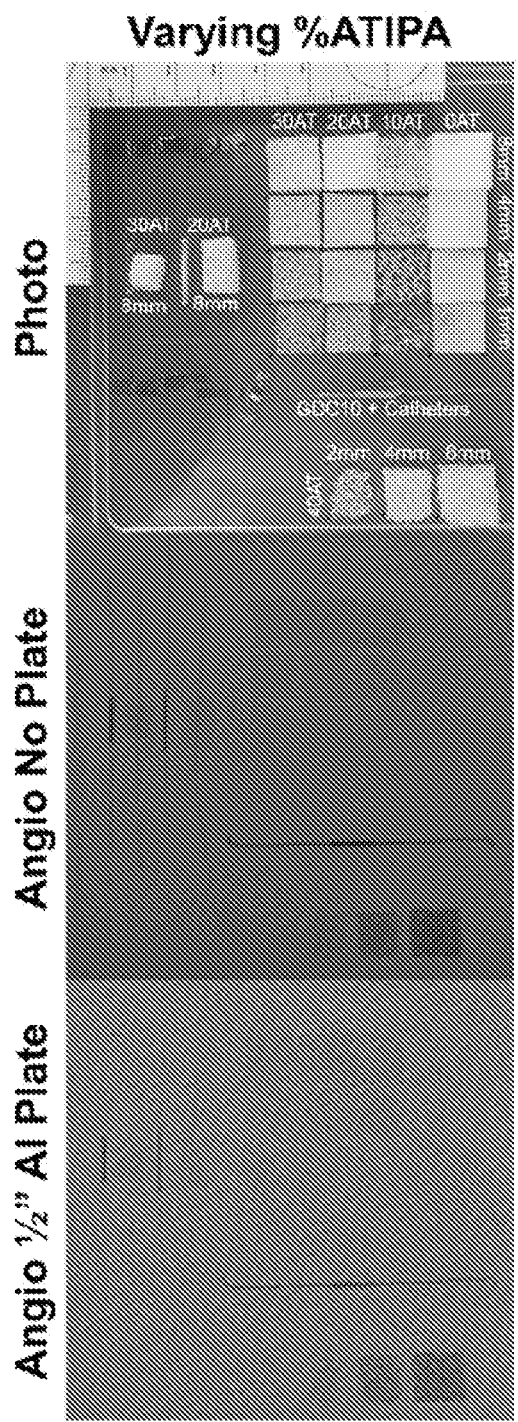
FIG. 17: Imaging frame including foam samples with varying ATIPA content at varying thickness; platinum embolic coils (GDC10) and catheter segments for radiodensity reference; and 8 mm diameter foam cylinder device prototypes in expanded and compressed states. Samples were imaged with a camera, unimpeded angiography, and angiography through a ½" aluminum human skull analog.

FIG. 17 summarizes the x-ray visibility of low density foams with varying ATIPA content. The foams with 10-30 eq % ATIPA demonstrate comparable x-ray visibility because the blowing ATIPA reaction resulted in lower material density at higher contrast agent loading. These opposing trends resulted in comparable iodine content within the same expanded sample path length.

The 8 mm cylindrical peripheral embolization prototypes demonstrated visibility in their expanded state, even when imaged through the skull analog. When radially crimped, these materials demonstrated visibility comparable to commercially available embolic platinum coils. Radial compression also compensates for differences in bulk material density, revealing differences in x-ray visualization for samples with varying ATIPA content. For example, the radially compressed 30AT sample is noticeably more visible than the 20AT sample when imaged through the ½" Aluminum skull analog.

Figure 18:
FIG. 18: Imaging frame including 20 eq % ATIPA foam samples with varying densities and thickness; a platinum embolic coil (GDC10) for radiodensity reference; and 2 mm diameter foam cylinder device prototypes in expanded and crimped states. Samples were imaged with a camera, unimpeded angiography, and angiography through a ½" aluminum human skull analog.

FIG. 18 details foams with a fixed 20 eq % ATIPA composition at varying density. Increasing material density results in increased material visualization, with the densest foam exhibiting visibility at just 1 mm thickness, even through the skull analog. The 2 mm neurovascular prototypes displayed limited visibility, even when axially crimped.

To address the limited material visibility at the neurovascular device scale, embodiments incorporate foams with higher ATIPA percentages. Alternatively, some embodiments employ a combinatory approach of chemical opacification and tungsten nanoparticulate loading to achieve unprecedented levels of SMP foam visualization at neurovascular device scales. Based on the tensile testing data in the previous section, an ATIPA composite with tungsten nanoparticulate stress concentrators has a higher fracture toughness than the traditional non-visible SMP foam. This maintains the existing acceptable risk level for undesired embolic particulates, while affording excellent x-ray visualization during device implantation.

DSC

Figure 19:
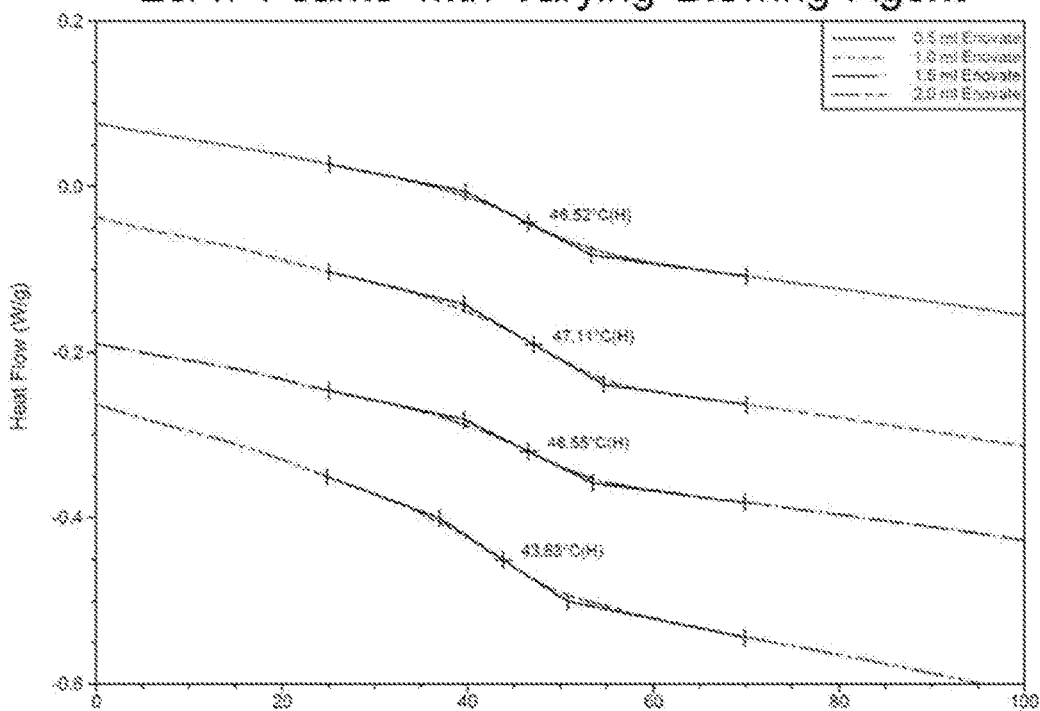
FIG. 19: Dry DSC thermograms showing minimal change in dry $T_g$ for foams with varying density due to changes in physical blowing agent (Enovate®) volume.

Differential scanning calorimetry was used to determine compositional effects on Tg and the breadth of thermal transitions. This data is important input for developing materials that are tuned to specific device design criteria, including foam expansion rate. FIG. 19 illustrates consistent thermal properties for foams with varying density due to physical blowing agent, further supporting the ability to control foam morphology independent of transition temperature. Lowering the foam density enables more material to crimp to a cross section that is deliverable through a catheter. This allows for larger volumetric expansion in-vivo and more effective filling to facilitate occlusion.

Figure 20:
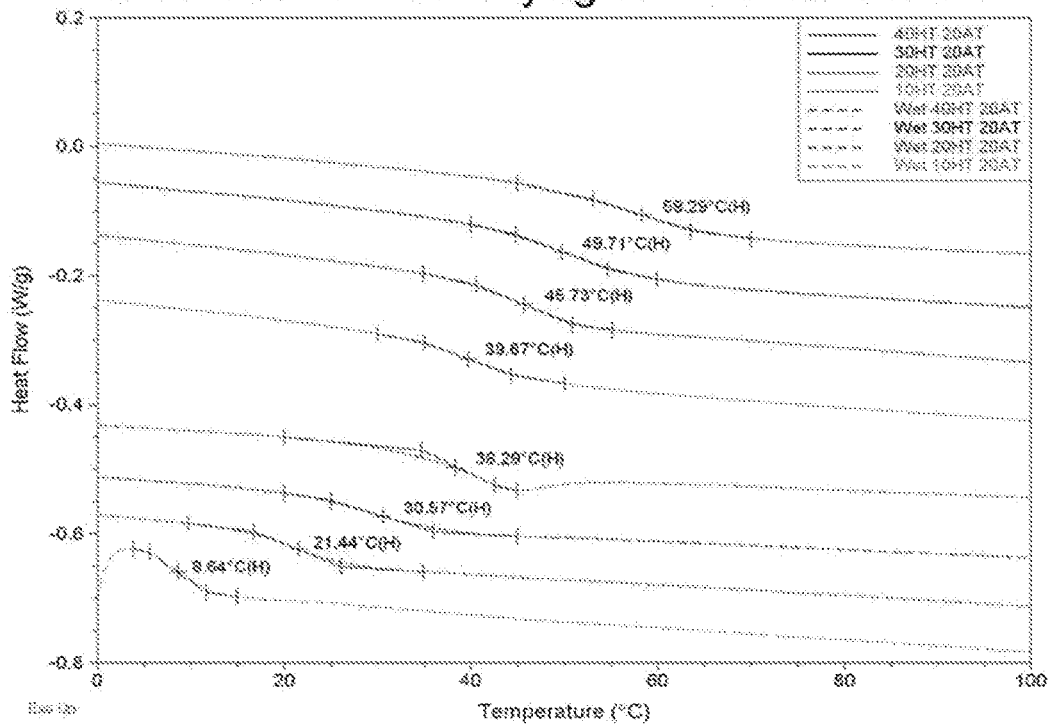
FIG. 20: DSC thermograms for dry and moisture plasticized 20 eq % ATIPA foams with varying HT content.

FIG. 20 shows incremental control over both dry and moisture plasticized Tg based on the HT composition. Increasing the molar ratio of the trifunctional HT monomer increases the crosslink density to make the polymer structure more rigid and raise the glass transition. For each composition, the wet and dry transitions are positioned on either side of body temperature (37° C.), enabling passive material expansion once implanted in the body. Based on these thermograms, the 20HT, 30HT, and 40HT compositions were chosen for further analysis towards device development. The 10HT composition was determined to have a dry transition too low for sufficient working times at the neurovascular device prototype scale but is applicable in some embodiments.

Both the transition temperature value and the breadth of transition increase with increasing HT content. As seen in the lower left corner of the figure, fully plasticized 10HT compositions still contained sufficient water content to register water freezing in the thermogram.

Figure 21:
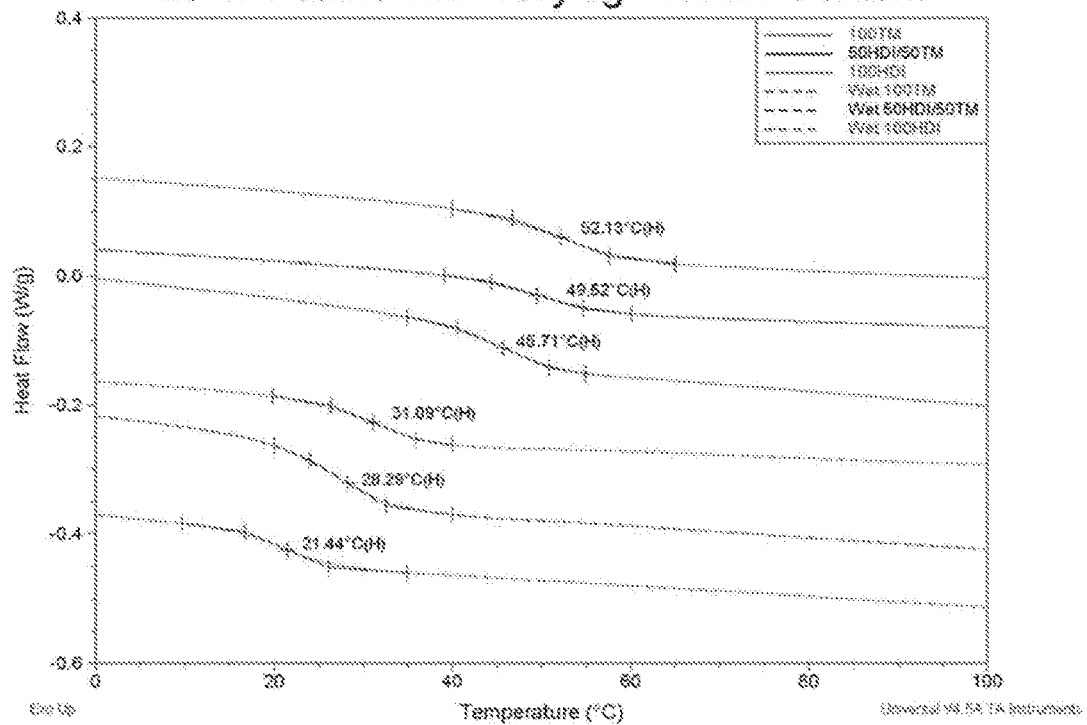
FIG. 21: Thermograms for dry and moisture plasticized 20 eq % ATIPA foams with varying isocyanate content.

Although less significant, changing the isocyanate content also enabled control over Tg (FIG. 21). Instead of altering crosslink density, increasing the molar ratio of TMHDI increased the rigidity of polymer chains between crosslinks. In addition to increasing Tg, higher TMHDI content is also anticipated to increase the bulk hydrophobicity of the material to reduce the moisture plasticization rate of the material and overall foam expansion time.

Figure 22:
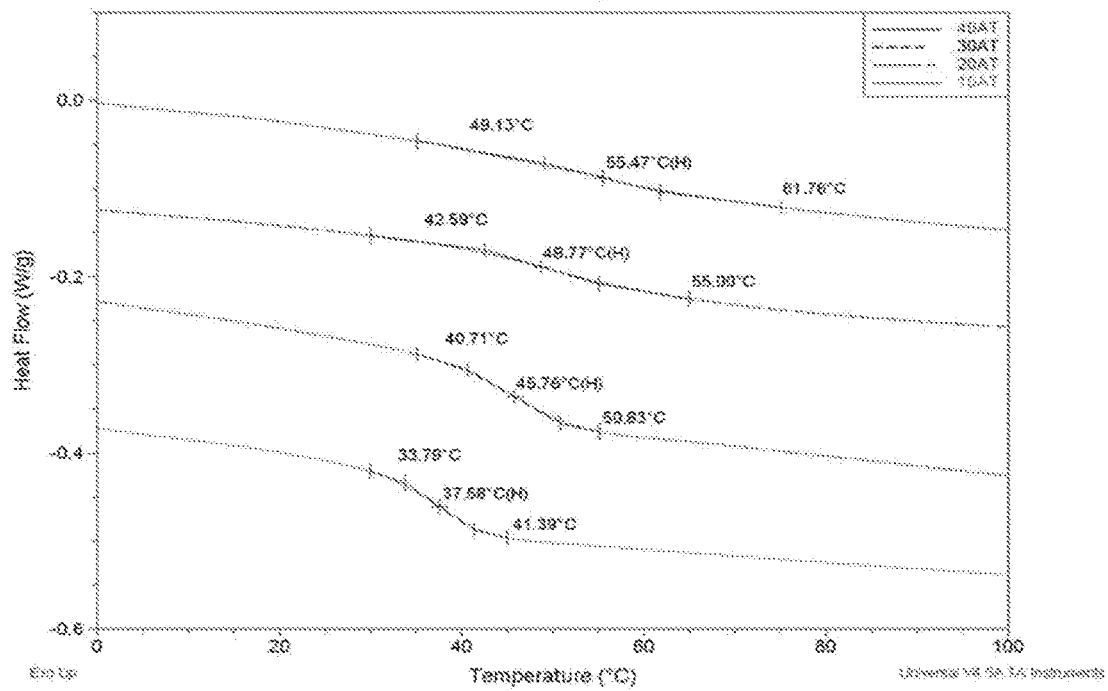
FIG. 22: Thermograms for dry foams with varying eq % of ATIPA.

Thermograms depicting increasing ATIPA composition are illustrated in FIG. 22. In addition to increasing Tg, there are also significant increases in transition breadth. The transition also becomes much less defined. These changes in the thermogram profile motivated further DMA analysis for these select compositions, except for the 40AT composition that was too brittle for sufficient analysis or prototyping.

DMA

Figure 23:
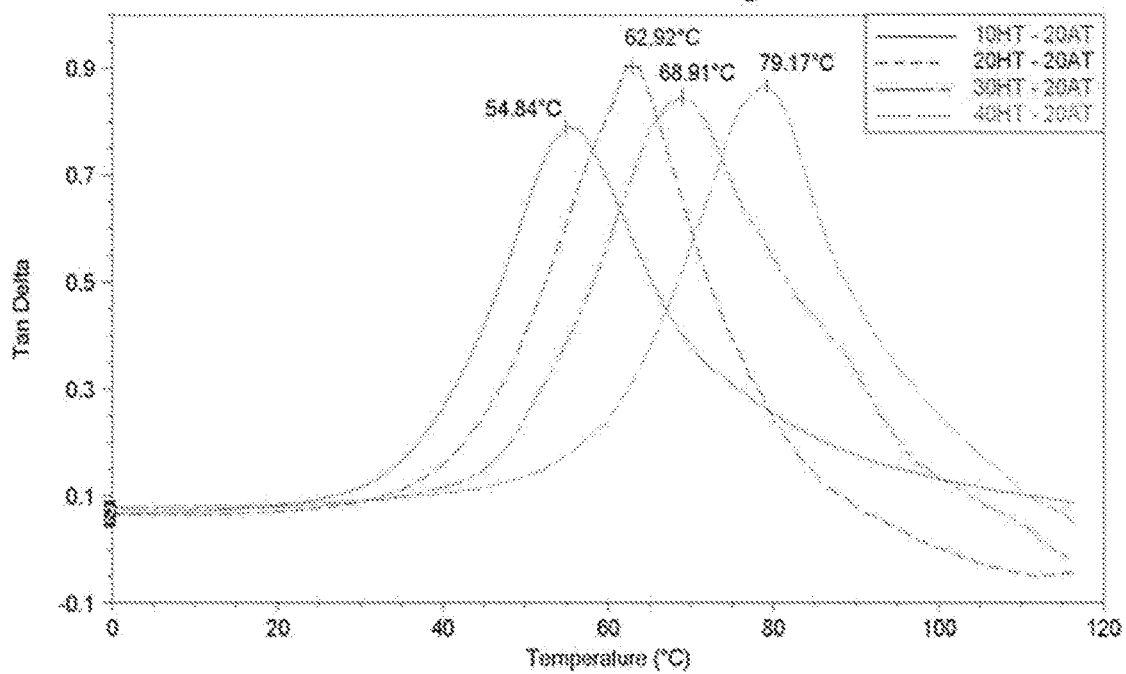
FIG. 23: Tangent delta plots from compression DMA of dry 20 eq % ATIPA foams with varying HT composition.

When comparing FIGS. 23 and 19, peak Tan δ values are approximately 20° C. higher than DSC dry Tg values. However, the incremental differences in each composition are comparable. This DMA data further supports increasing Tg with increasing HT content.

Figure 24:
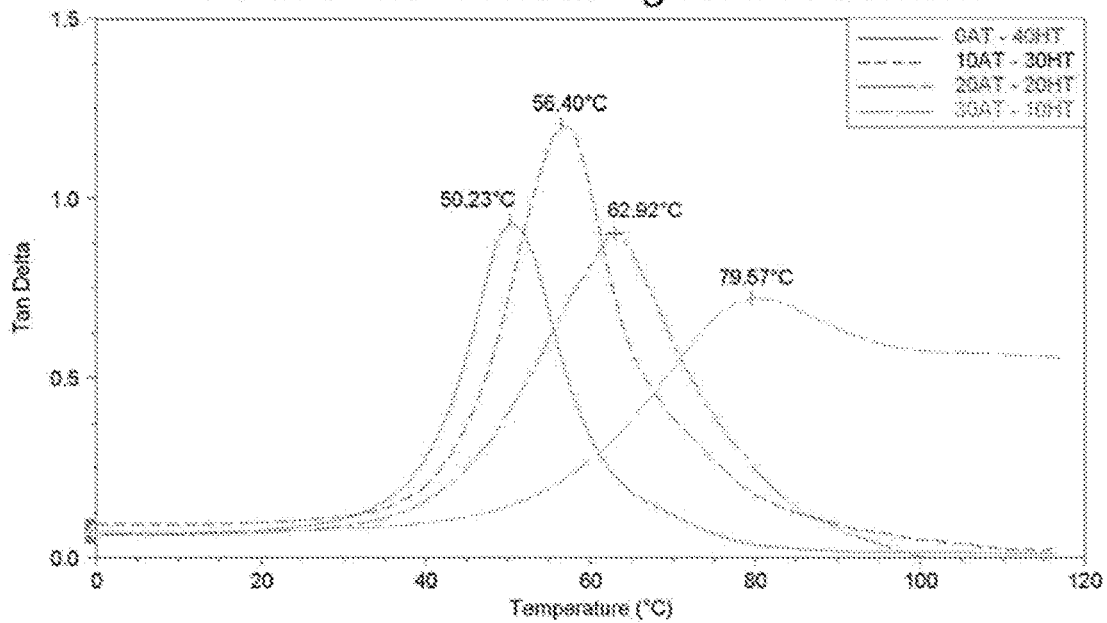
FIG. 24: Tangent delta plots for compression DMA of dry foams with varying ATIPA composition.

Tangent δ plots in FIG. 24 illustrate Tg values 20-30° C. higher than dry DSC values in FIG. 21. The DMA curves also show a similar trend with increasing Tg and transition breadth with increasing ATIPA content. Most interesting is the shape of the 30AT composition curve. Although a signal peak is evident, the Tan δ signal does not return to baseline after the thermal transition. This is indicative of a dampening material with a low rubbery modulus, which are poor shape memory characteristics suitable for some embodiments but not for others. Based on these results, foam compositions for device prototyping were chosen based on the maximum inherent solubility of ATIPA in the other polyol constituents without solvent. This maximum is in the 20-25 ATIPA eq % range, depending on the composition.

Unconstrained Expansion

Figure 25:
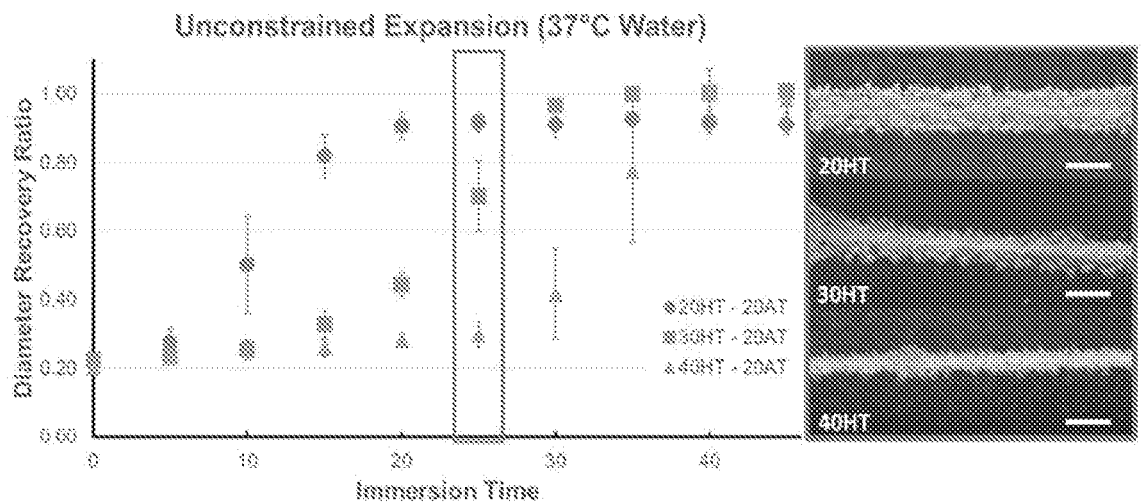
FIG. 25: Left—Unconstrained expansion profiles of 2 mm diameter foams compressed over a 0.006" wire and submerged in 37° C. water. Right—Snapshots of foams after 25 minutes of immersion.

Foams with varying HT content displayed volumetric recovery behavior in body temperature water that is congruent with Tg trends. As seen in FIG. 25, compositions with higher HT content and higher Tg took longer to expand. The 30 and 40 eq % HT compositions also showed higher average volumetric recovery (99%) when compared to 20 eq % HT foams with a lower crosslink density (91%).

This data shows embodiments are suitable for a neurovascular embolization device design. With an average crimped diameter of 0.0196"±0.001", these prototypes are close to fitting within a 0.021" microcatheter lumen with a target minimum tolerance of 0.002". Modifications to the blowing agent and surfactant composition can decrease the bulk foam density for smaller crimped dimensions, in addition to using a smaller diameter device backbone filament.

These expansion profiles show an estimated minimum working time of 10 minutes for the 30HT composition and 15 minutes for the 40HT composition. These default expansion times are already in the clinically acceptable range without employing surface coatings to modulate moisture plasticization.

FTIR-ATR

Figure 26:
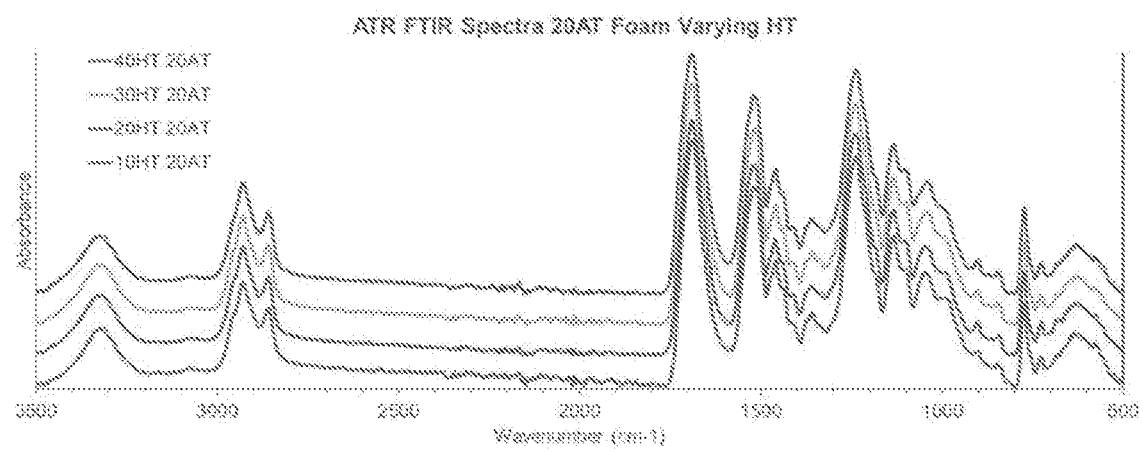
FIG. 26: ATR FTIR spectra for 20AT foams with increasing HT content.

Infrared spectra in FIG. 26 do not exhibit significant changes with increasing HT content. However, these spectra do show peaks characteristic of polyurethane foams. The broad peak centered at 3310 cm-1 highlights N—H vibrations. Peaks at 2852 cm-1 and 2923 cm-1 are from symmetric and asymmetric C—H stretching from the MPD methyl group. It is worthy to note the lack of an unreacted NCO peak at 2260 cm-1. At 1685 cm-1, the C=O urethane peak is significantly right shifted due to hydrogen bonding. This is congruent with hydrogen bonded urethane peaks in other polyurethane SMP foams with relatively low molecular weights between crosslinks when compared to segmented polyurethanes. A strong hydrogen bonded Amide II peak can be seen at 1515 cm-1.

Figure 27:
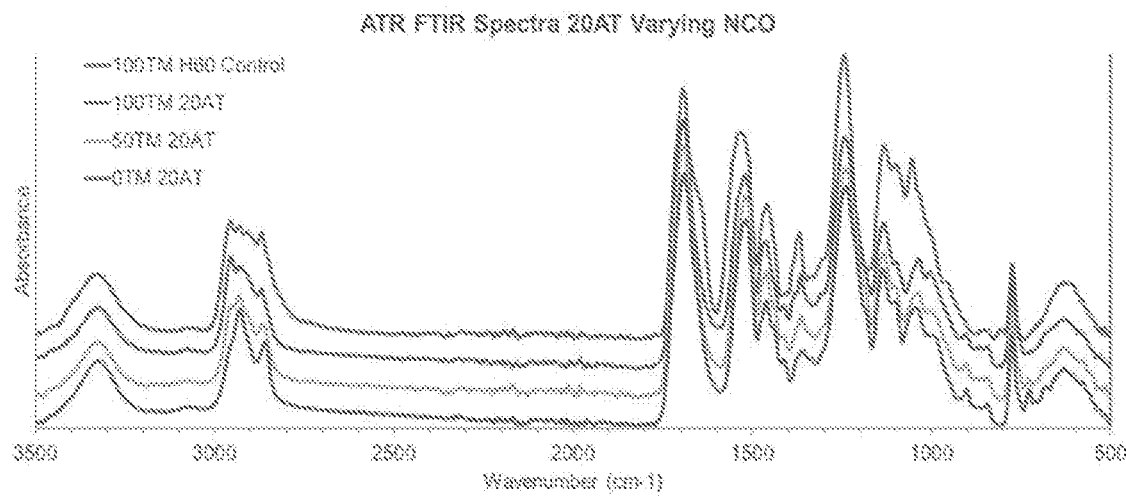
FIG. 27: ATR FTIR spectra for 20AT foams with increasing TMHDI content. Non-visible 100™ H60 control foam spectra included for comparison.

20 eq % ATIPA foam spectra with increasing TMHDI content are shown in FIG. 27. A non-visible 100™ H60 foam is also included for comparison. Increased methylation with increasing TMHDI content is evident due to peak broadening between 2800-3000 cm-1. Compared to the non-visible foam, ATIPA foams do not have a prominent urea shoulder at 1650 cm-1 due to the lack of H2O chemical blowing used in traditional polyurethane foaming.

Figure 28:
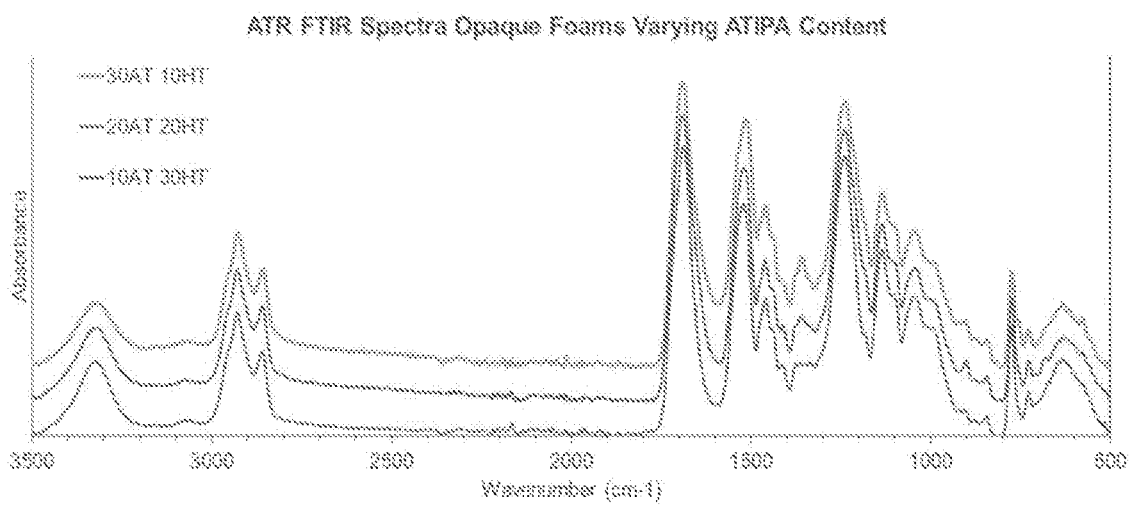
FIG. 28: ATR FTIR spectra for foams with increasing ATIPA content at fixed theoretical crosslink density.

Compositions with increasing ATIPA content, FIG. 28, show a broadening urea shoulder due to higher $NH_2$ reactive groups during synthesis. This differs from the urea content present in traditional polyurethane urea foams that use water as a chemical blowing agent. Increased ATIPA content is also evident by peaks at 1360 cm-1 and a shoulder at 770 cm-1.

In this work, chemically modified shape memory polymer foams with inherent x-ray visualization were successfully fabricated through the incorporation of triiodobenzene containing monomers. Altering the molar ratios of the other constituent monomers also demonstrated functional changes in these polymer scaffolds that make embodiments suitable to function as embolic medical devices.

Example embodiments are now described.

Example 1 includes a medical device containing a thermoset shape memory polymer foam that can be programmed into a metastable secondary shape and stimulated to recover to its primary shape where the shape memory polymer foam contains triiodobenzene monomers for direct x-ray visualization.

Example 2 includes the device of example 1 where the triiodobenzene monomer is selected from 5-amino-2,4,6-triiodoisophthalic acid, diatrizoic acid, iohexol, triiodophenol.

Example 3 includes the device of example 1 where the monomer 5-amino-2,4,6-triiodoisophthalic acid is used as the crosslinker, blowing agent, and x-ray contrast agent for the shape memory polymer.

Example 4 includes the device of example 1 where the shape memory polymer foam composition contains at least one of the following aliphatic polyols: 1,2,6-hexanetriol, 2-butyl-2-ethyl-propanediol, 3-methyl-1,5-pentanediol, di ethyl ene glycol, tri ethyl ene glycol, triethanolamine, tetrakis-hydroxypropyl ethylenediamine, glycerol, trimethylolpropane, trimethylolmethane, and 1,2,4-butanetriol.

Example 5 includes the device of example 1 where the shape memory polymer foam composition contains at least one of the following aliphatic diisocyanates: hexamethylene diisocyanate, trimethylhexamethylene diisocyanate, isophorone diisocyanate.

Example 6 includes the device of example 1 where the shape memory polymer contains 1,2-diaminopropane, 2,2-Dimethyl-1,3-propanediamine, 1,8-Diaminooctane, 3-Amino-1,2-propanediol, 2-Amino-2-methyl-1,3-propanediol, or other aliphatic monomers containing multiple amine or alcohol functional groups.

Example 7 includes the device of example 1 where the shape memory polymer foam composition contains at least one of the following aromatic diisocyanates; 1,3,4-triisocyanato-2,4,6-trimethylbenzene, toluene diisocyanate, methylene diphenyl diisocyanate.

Example 8 includes the device of example 1 where the shape memory polymer foam is a poly(urethane-urea-amide).

Example 9 includes the device of example 1 where the compressed shape memory polymer foam contains 50-500 mg/ml of Iodine.

However, other embodiments may include 100, 200, 300, 400 or more mg/ml of Iodine.

Example 10 includes the device of example 1 where the shape memory polymer foam has a dry glass transition temperature between 40-80 C.

However, other embodiments are between 40 and 100 or 40 and 90 or 40 and 70 or 40 and 60 C.

Example 11 includes the device of example 1 where the shape memory polymer foam has a moisture plasticized glass transition temperature onset below 37 C.

In other embodiments the moisture plasticized glass transition temperature onset is below 40, 39, 38, 37, 36, 35, 34 C.

Example 12 includes the device of example 1 where the secondary shape of the device is radially compressed geometry that allows minimally invasive delivery through a catheter.

Example 13 includes a method of manufacturing a thermoset shape memory polymer foam that can be programmed into a metastable secondary shape and stimulated to recover to its primary shape where the shape memory polymer foam contains triiodobenzene monomers for direct x-ray visualization.

Example 14 includes the method of example 13 where the thermoset shape memory polymer foam is fabricated through the combination of 5-amino-2,4,6-triiodoisophthalic acid, 1,2,6-hexanetriol, 2-butyl-2-ethyl-propanediol, 3-methyl-1,5-pentanediol, an aliphatic diisocyanate, a physical blowing agent, and surfactants.

Example 15 includes the device of example 1 where the shape memory polymer foam composition contains polycaprolactone (PCL).

Example 1a includes a system comprising: a thermoset shape memory polymer (SMP) foam that is covalently bonded to iodine; wherein (a) the SMP foam is configured to expand from a compressed secondary state to an expanded primary state in response to thermal stimulus, and (b) the SMP foam is a poly(urethane-urea-amide).

Example 2a includes the system of example 1a wherein the SMP foam is radiopaque.

Example 3a includes the system of example 2a wherein the iodine is included in a triiodobenzene monomer.

Example 4a includes the system of example 3a wherein the triiodobenzene monomer includes at least one of (a) 5-amino-2,4,6-triiodoisophthalic acid (ATIPA), (b) diatrizoic acid, (c) iohexol, and (d) triiodophenol.

Example 5a includes the system of example 4a wherein the triiodobenzene monomer includes ATIPA.

Example 6a includes the system of example 5a wherein the ATIPA crosslinks polymer chains of the SMP foam.

Another version of example 6a includes the system of example 5a wherein (a) the ATIPA crosslinks polymer chains of the SMP foam, and (b) another crosslinking agent crosslinks polymer chains of the SMP foam.

Example 7a includes the system of example 3a wherein the SMP foam includes at least one of platinum, tungsten, and tantalum, the at least one of platinum, tungsten, and tantalum being physically bound within the SMP foam.

Example 8a includes the system of example 7a wherein the at least one of platinum, tungsten, and tantalum is not chemically bound to the SMP foam.

Example 9a includes the system of example 3a comprising a backbone that traverses the SMP foam, wherein the backbone includes at least one of a polymer filament and a metal.

Example 10a includes the system of example 9a wherein the backbone includes a polymer filament and no metal.

In other version of Example 10a the backbone includes a polymer but no metal. In other version of Example 10a the backbone includes a majority % of polymer and a minority % of metal.

Example 11a includes a method comprising: providing a triiodobenzene monomer; providing an aliphatic monomer comprising at least one of (a)(i) multiple amine functional groups, (a)(ii) multiple alcohol functional groups, and (a)(iii) multiple carboxylic acid functional groups; providing a diisocyanate; mixing the triiodobenzene monomer, the aliphatic monomer, and the diisocyanate into a solution; forming a thermoset shape memory polymer (SMP) foam from the solution.

Example 12a includes the method of example 11a wherein: triiodobenzene monomer includes a first member selected from the group consisting of 5-amino-2,4,6-triiodoisophthalic acid (ATIPA), diatrizoic acid, iohexol, and triiodophenol; the aliphatic monomer includes a second member selected from the group consisting of 1,2,6-hexanetriol (HT); 2-butyl-2-ethyl-propanediol (BEP); 3-methyl-1,5-pentanediol (MPD); diethylene glycol (DEG); triethylene glycol (TEG); triethanolamine (TEA); tetrakis-hydroxypropyl ethylenediamine (HPED); glycerol; trimethylolpropane; trimethylolmethane; 1,2,4-butanetriol; 1,2-diaminopropane; 2,2-Dimethyl-1,3-propanediamine; 1,8-Diaminooctane; 3-Amino-1,2-propanediol; 2-Amino-2-methyl-1,3-propanediol; 1,3-Diamino-2-propanol; and aspartic acid; the diisocyanate includes a third member selected form the group consisting of hexamethylene diisocyanate (HDI); trimethylhexamethylene diisocyanate (TMHDI); isophorone diisocyanate; 1,3,4-triisocyanato-2,4,6-trimethylbenzene; toluene diisocyanate; and methylene diphenyl diisocyanate.

Example 13a includes the method of example 12a wherein the second member is selected from the group consisting of HT; BEP; MPD; DEG; TEG; TEA; HPED; glycerol; trimethylolpropane; trimethylolmethane; and 1,2,4-butanetriol.

Example 14a includes the method of example 12a wherein the second member is selected from the group consisting of 1,2-diaminopropane; 2,2-Dimethyl-1,3-propanediamine; 1,8-Diaminooctane; 3-Amino-1,2-propanediol; and 2-Amino-2-methyl-1,3-propanediol.

Example 15a includes the method of example 12a wherein the third member is selected form the group consisting of HDI; TMHDI; and isophorone diisocyanate.

Example 16a includes the method of example 12a wherein the third member is selected form the group consisting of elected form the group consisting of 1,3,4-triisocyanato-2,4,6-trimethylbenzene; toluene diisocyanate; and methylene diphenyl diisocyanate.

Example 17a includes the method of example 12a wherein the first member is ATIPA.

Another version of Example 17a includes the method of example 12a wherein the first member is ATIPA and the ATIPA constitutes between 20 and 30% MW of the first and second members.

Example 18a includes the method of example 12a comprising crosslinking the second and third members with the first member.

Example 19a includes the method of example 18a wherein forming the SMP foam from the solution comprises utilizing the first member as a chemical blowing agent.

Example 20a includes the method of example 12a wherein the aliphatic monomer includes a fourth selected from the group consisting of HT; BEP; MPD; DEG; TEG; TEA; HPED; glycerol; trimethylolpropane; trimethylolmethane; 1,2,4-butanetriol; 1,2-diaminopropane; 2,2-Dimethyl-1,3-propanediamine; 1,8-Diaminooctane; 3-Amino-1,2-propanediol; 2-Amino-2-methyl-1,3-propanediol; 1,3-Diamino-2-propanol; and aspartic acid;

Example 21a includes a system comprising: an iodine containing thermoset open-cell shape memory polymer (SMP) foam that is x-ray visible; wherein (a) the SMP foam is configured to expand from a compressed secondary state to an expanded primary state in response to thermal stimulus, (b) the SMP foam is a poly(urethane-urea-amide).

Whether something is "x-ray visible" or "radiopaque" is judged according to a person of ordinary skill in the art, such as a neurosurgeon or interventional neuroradiologist that routinely treats aneurysms using imaging, such as fluoroscopy or angiography. While x-ray power may vary depending on the imaging machine used and the like, a person of ordinary skill in the art will still understand whether a foam is visible under normal clinical conditions such that the foam is discernable from the surrounding anatomy.

Example 22a includes the system of example 21a wherein the iodine is included in a triiodobenzene monomer and the iodine is covalently bonded within a polymer network of the SMP foam.

Another version of Example 22a includes the system of example 21a wherein the iodine is included in a triiodobenzene monomer and the iodine is physically incorporated within the SMP foam.

Another version of Example 22a includes the system of example 21a wherein the iodine is included in at least one triiodobenzene monomer and the iodine is both: (a) covalently bonded within a polymer network of the SMP foam, and (b) physically incorporated, but not chemically bonded, within the SMP foam.

Example 23a includes the system of example 22a wherein the SMP foam in the secondary state contains between 50 and 500 mg/ml of Iodine.

However, other embodiments the SMT foam in the secondary state may include between 50 and 100, 100 and 200, 200 and 300, 300 and 400 or more mg/ml of Iodine.

Example 24a includes the system of example 23a wherein: the SMP foam in its primary state has a density of less than 0.1 g/cc; the SMP foam has a dry glass transition temperature (Tg) between 30 and 100 degrees C.

Tg calculation is described above in the discussion for Example 24a.

Another version of Example 24a includes the system of example 23a wherein: the SMP foam in its primary state has a density of less than 0.1 g/cc; the SMP foam has a dry glass transition temperature (Tg) between 30 and 100 degrees C.; and the SMP foam lacks a Fourier transform infrared spectroscopy (FTIR) urea peak at 1650 cm-1.

Other versions of Example 24a have a density of less than 0.09, 0.08, 0.07, 0.06, or 0.05 g/cc.

Example 25a includes the system of example 22a wherein the SMP foam comprises polycaprolactone (PCL).

Example 26a includes the system of example 3a comprising at least one of a stent and a flow diverter and the SMP foam is coupled to the at least one of a stent and a flow diverter.

Example 27a includes the system of example 22a comprising: a fully encapsulated kit, a flexible conduit; and a pusher rod; wherein the flexible conduit includes the SMP foam within the flexible conduit, the SMP foam is coupled to the pusher rod, at least a portion of the pusher rod is included within the flexible conduit.

For instance, the kit may be a sealed sterilized kit that is shipped to a medical facility. The conduit may include some form of catheter.

Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. A system comprising:
   a radiopaque thermoset shape memory polymer (SMP) foam that is covalently bonded to iodine;
   wherein (a) the SMP foam is configured to expand from a compressed secondary state to an expanded primary state in response to thermal stimulus, (b) the SMP foam is a poly(urethane-urea-amide), (c) the iodine is included in 5-amino-2,4,6-triiodoisophthalic acid (ATIPA), and (d) the SMP foam does not include a tertiary amine.

2. The system of claim 1 wherein the ATIPA crosslinks polymer chains of the SMP foam.

3. The system of claim 1 wherein the SMP foam includes at least one of platinum, tungsten, tantalum, or combinations thereof, the at least one of platinum, tungsten, tantalum, or combinations thereof being physically bound within the SMP foam.

4. The system of claim 3 wherein the at least one of platinum, tungsten, tantalum, or combinations thereof is not chemically bound to the SMP foam.

5. The system of claim 1 comprising a backbone that traverses the SMP foam, wherein the backbone includes at least one of a polymer filament, a metal, or combinations thereof.

6. The system of claim 5 wherein the backbone includes a polymer filament and no metal.

7. A system comprising:
   an iodine containing thermoset open-cell shape memory polymer (SMP) foam that is x-ray visible;
   wherein (a) the SMP foam is configured to expand from a compressed secondary state to an expanded primary state in response to thermal stimulus, (b) the SMP foam is a poly(urethane-urea-amide), (c) the iodine is derived from 5-amino-2,4,6-triiodoisophthalic acid (ATIPA), and (d) the SMP foam does not include a tertiary amine.

8. The system of claim 7 wherein the iodine is covalently bonded within a polymer network of the SMP foam.

9. The system of claim 7 wherein:
the SMP foam in its primary state has a density of less than 0.1 g/cc;
the SMP foam has a dry glass transition temperature (Tg) between 30 and 100 degrees C.; and
the SMP foam lacks a Fourier transform infrared spectroscopy (FTIR) urea peak at 1650 cm$^{-1}$.

10. The system of claim 7 wherein the SMP foam comprises polycaprolactone (PCL).

11. A method comprising:
providing 5-amino-2,4,6-triiodoisophthalic acid (ATIPA);
providing at least one aliphatic monomer comprising at least one of (a)(i) multiple amine functional groups, (a)(ii) multiple alcohol functional groups, (a)(iii) multiple carboxylic acid functional groups, or (a)(iv) combinations thereof;
providing a diisocyanate;
mixing the ATIPA, the at least one aliphatic monomer, and the diisocyanate into a solution;
forming a radiopaque thermoset open-cell shape memory polymer (SMP) foam from the solution;
wherein the SMP foam: (a) includes iodine that is derived from the ATIPA, (b) is configured to expand from a compressed secondary state to an expanded primary state in response to thermal stimulus, (c) is a poly(urethane-urea-amide), and (d) does not include a tertiary amine.

12. The method of claim 11 wherein:
the at least one aliphatic monomer includes at least one of 1,2,6-hexanetriol (HT); 2-butyl-2-ethyl-propanediol (BEP); 3-methyl-1,5-pentanediol (MPD); diethylene glycol (DEG); triethylene glycol (TEG); glycerol; trimethylolpropane; trimethylolmethane; 1,2,4-butanetriol; 1,2-diaminopropane; 2,2-Dimethyl-1,3-propanediamine; 1,8-Diaminooctane; 3-Amino-1,2-propanediol; 2-Amino-2-methyl-1,3-propanediol; 1,3-Diamino-2-propanol; aspartic acid, or combinations thereof;
the diisocyanate includes at least one of hexamethylene diisocyanate (HDI); trimethylhexamethylene diisocyanate (TMHDI); isophorone diisocyanate; 1,3,5-triisocyanato-2,4,6-trimethylbenzene; toluene diisocyanate; methylene diphenyl diisocyanate, or combinations thereof.

13. The method of claim 12 comprising crosslinking polymer chains of the SMP foam with the ATIPA.

14. The method of claim 12 wherein the at least one aliphatic monomer includes at least two of HT; BEP; MPD; DEG; TEG; glycerol; trimethylolpropane; trimethylolmethane; 1,2,4-butanetriol; 1,2-diaminopropane; 2,2-Dimethyl-1,3-propanediamine; 1,8-Diaminooctane; 3-Amino-1,2-propanediol; 2-Amino-2-methyl-1,3-propanediol; 1,3-Diamino-2-propanol; or aspartic acid.

* * * * *

UNITED STATES PATENT AND TRADEMARK OFFICE
CERTIFICATE OF CORRECTION

PATENT NO. : 11,407,851 B2
APPLICATION NO. : 16/465555
DATED : August 9, 2022
INVENTOR(S) : Nash et al.

Page 1 of 1

It is certified that error appears in the above-identified patent and that said Letters Patent is hereby corrected as shown below:

In the Claims

Column 22:
Line 42, "included in" should be --derived from--.

Signed and Sealed this
Thirteenth Day of September, 2022

Katherine Kelly Vidal
*Director of the United States Patent and Trademark Office*